United States Patent [19]
Wang et al.

[11] Patent Number: 5,494,038
[45] Date of Patent: Feb. 27, 1996

[54] APPARATUS FOR ULTRASOUND TESTING

[75] Inventors: Jianjun Wang, Columbus; Billy D. Cornelius, Powell; Lonnie R. Drayer, Gahanna, all of Ohio

[73] Assignee: Abbott Laboratories, Abbott Park, Ill.

[21] Appl. No.: 428,380

[22] Filed: Apr. 25, 1995

[51] Int. Cl.⁶ .............................. A61B 8/00; G01N 29/04
[52] U.S. Cl. ........................ 128/662.03; 73/644
[58] Field of Search ................. 128/660.01, 662.03; 73/644, 631

[56] References Cited

U.S. PATENT DOCUMENTS

| | | | |
|---|---|---|---|
| 3,721,227 | 3/1973 | Larson et al. | 128/662.05 |
| 3,946,599 | 3/1976 | Patt | 310/8.3 |
| 4,033,178 | 7/1977 | Holt et al. | 73/644 |
| 4,726,231 | 2/1988 | Tretout et al. | 73/644 |
| 4,796,632 | 1/1989 | Boyd et al. | 120/662.03 |
| 4,844,080 | 7/1989 | Frass et al. | 128/660.01 |
| 4,929,368 | 5/1990 | Baumoel | 252/11 |
| 4,961,176 | 10/1990 | Tanaka et al. | 128/660.01 X |
| 5,016,615 | 5/1991 | Driller et al. | 604/20 X |
| 5,123,281 | 6/1992 | Cox et al. | 73/644 |
| 5,214,343 | 5/1993 | Baumoel | 310/334 |
| 5,265,614 | 11/1993 | Hayakawa et al. | 128/662.03 |
| 5,280,722 | 1/1994 | Madaras | 73/588 |

FOREIGN PATENT DOCUMENTS 4237378  4/1994  Germany .

OTHER PUBLICATIONS

Ahvenainen et al., Lebensmittel Wissenschaft und Technologie, 22(5):268–272 (1989).
Ahvenainen et al., Lebensmittel Wissenschaft und Technologie, 22(6):382–386 (1989).
Wirtanen et al., International Journal Of Food Science And Technology, 26:313–324 (1991).
Gunasekaran et al., Food Technology, Dec. 1994, pp. 74–78.
NASA Tech Briefs, Dec. 1994, pp. 77–78.
Sales brochure for "The Aloka 620™", from Corometrics Medical Systen Inc., undated.
Advertisement for "Argus Class Large Size Scanning Systems" from Panametrics, undated.
Sales brochure from Sartorius Filters Inc.

*Primary Examiner*—Francis Jaworski
*Attorney, Agent, or Firm*—Lonnie R. Drayer

[57] ABSTRACT

The need for a highly viscous couplant gel or water spray to form an acoustical couple for ultrasound testing is eliminated by employing an ultrasound probe module. A porous membrane and an ultrasound probe cooperate to define a chamber which contains a liquid acoustical couplant. When pressure is applied to the liquid acoustical couplant it passes through the porous membrane. The porous membrane and chamber are disposed such that ultrasound signals going to or away from the ultrasound probe pass through the liquid acoustical couplant and porous membrane.

23 Claims, 18 Drawing Sheets

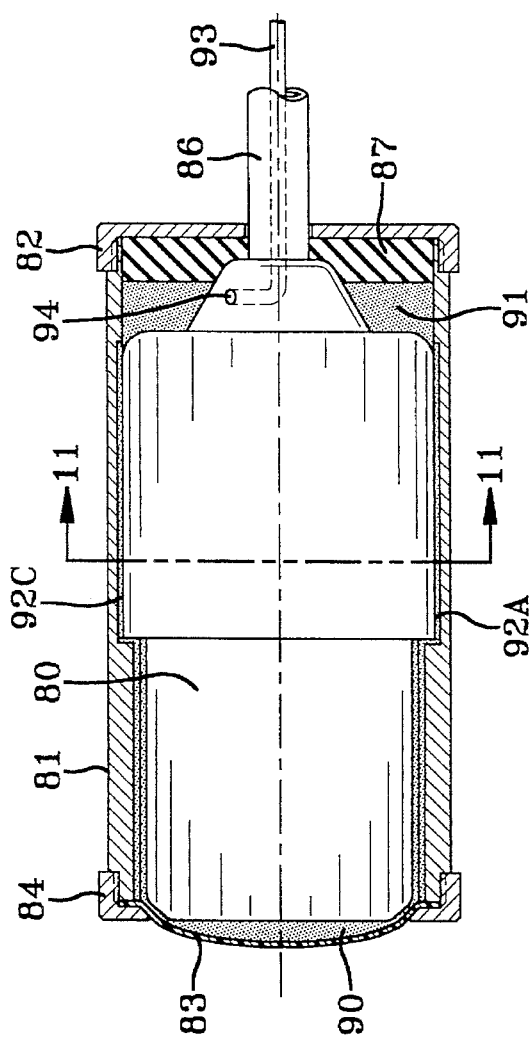
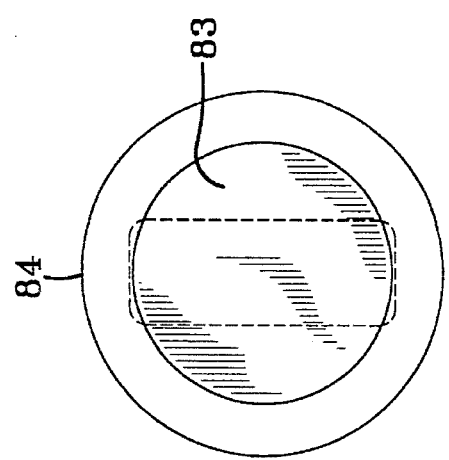
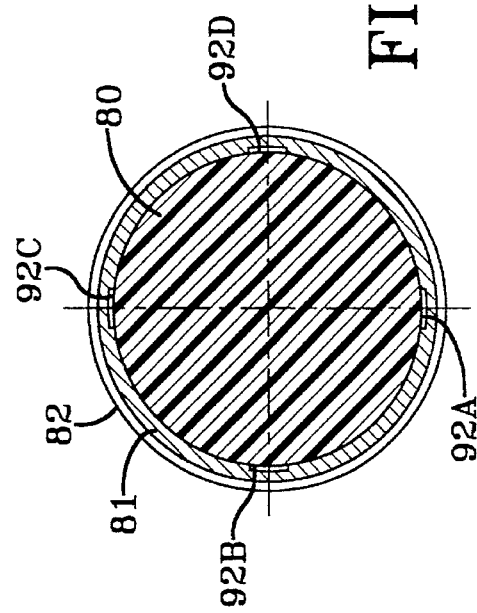
FIG-9
FIG-10
FIG-11

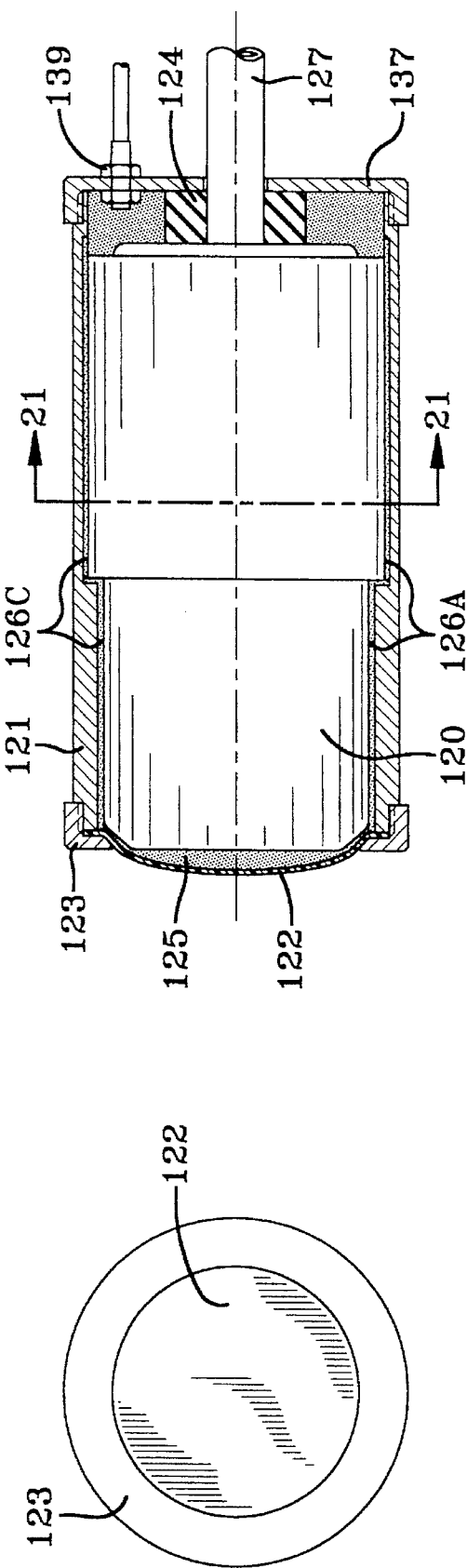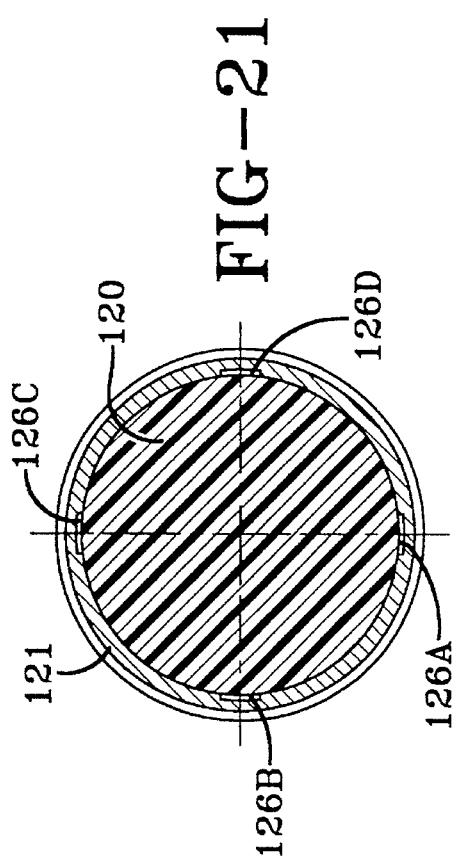
FIG-19
FIG-20
FIG-21

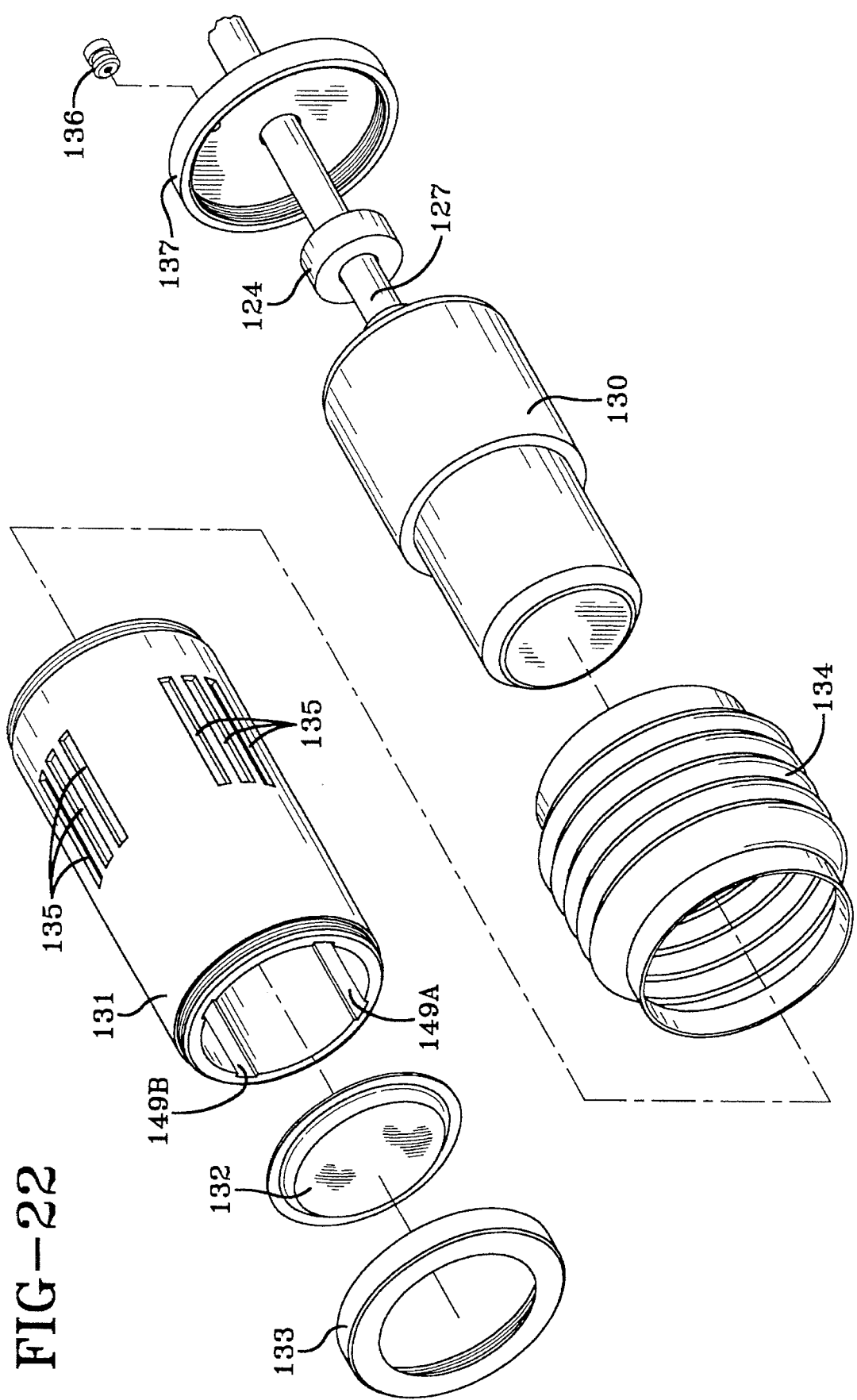

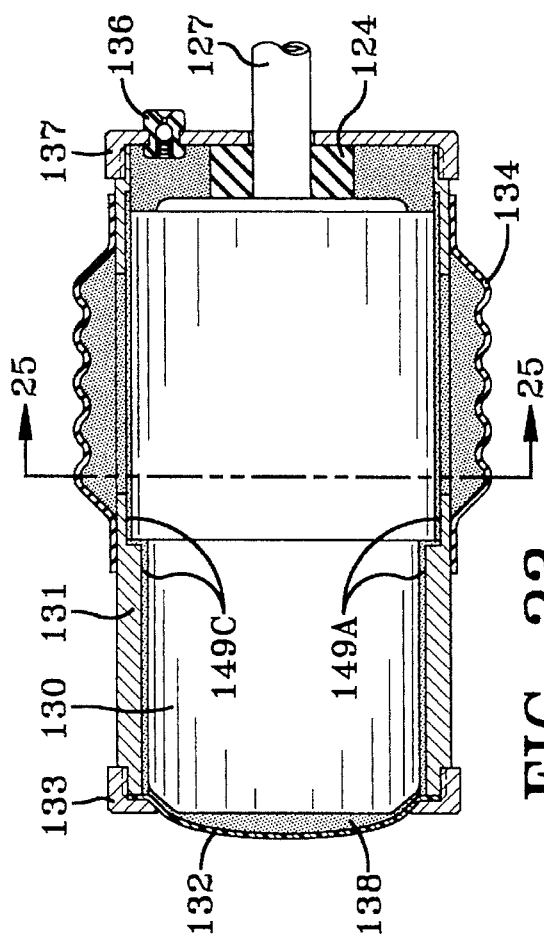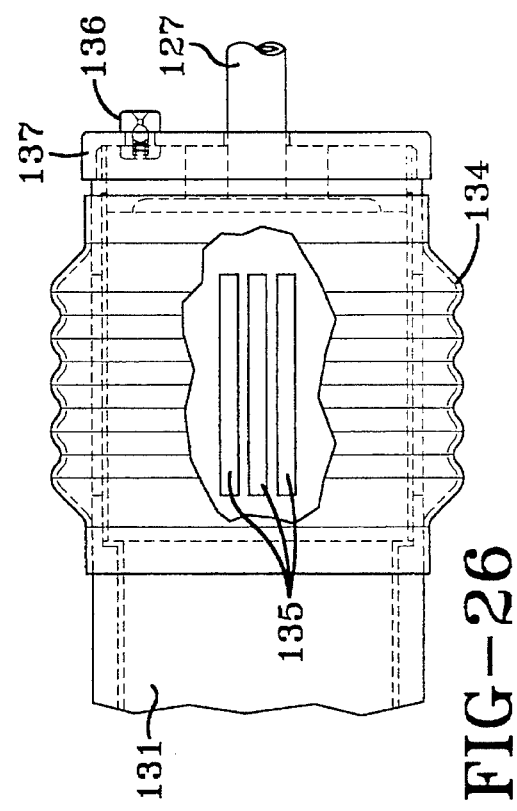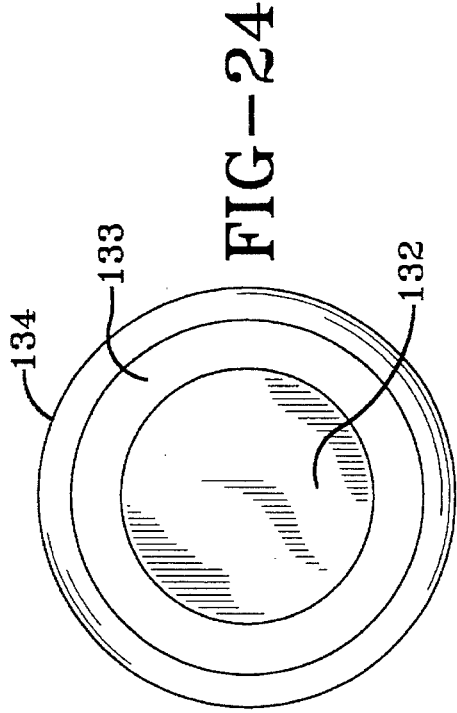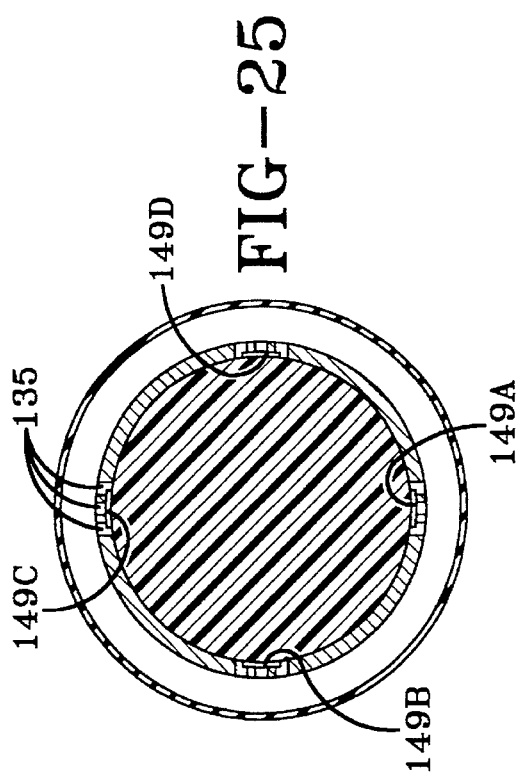

APPARATUS FOR ULTRASOUND TESTING

FIELD OF THE INVENTION

The present invention relates generally to an apparatus for use in the performance of ultrasound imaging and ultrasound pulse-echo testing, and more specifically to a device which eliminates the need for separately applying a couplant to the skin of a person, or surface of an object which will be subjected to ultrasound testing.

BACKGROUND OF THE INVENTION

Ultrasound imaging and pulse-echo technology has been widely used in the medical field for therapy, diagnostic testing and evaluating pregnancies. It has also been widely used for evaluating castings, forgings and other structures with regards to delamination, voids, cracks, weld integrity and other indicators of structural integrity. Furthermore, ultrasonic technology has application in evaluating seal integrity spoilage or contamination in food products.

A major factor in the successful application of ultrasound testing is the establishment of an interface between the ultrasound probe and the surface/skin of the item/person to achieve the best possible impedance match and minimize signal loss. This interface is commonly achieved by applying an ultrasound transmission gel to the surface/skin of the item/person which will receive the ultrasound waves, and then bringing an ultrasound probe into contact with the gel. A continuous flow of water between the surface of an object and an ultrasound probe which acts as a bridge for ultrasound waves has been employed as a couplant in industrial applications for evaluating structures. Immersion of the object being tested in water to act as a couplant is also commonly practiced.

Ultrasound transmission gels are available in squeeze bottles, foil packs, bulk containers and gel pads. These gels are relatively expensive, and their use is messy and labor intensive. The use of a liquid spray as an ultrasound couplant requires relatively sophisticated and expensive equipment, and of course the use of a liquid can be result in overflows and spills.

One approach to the elimination of gels or flowing liquids as acoustical couplants is a dry couplant pad made-of a compliant encapsulated epoxy material attached as a facing to an ultrasonic-transducer wedge. However, such a solid couplant material has a lower ultrasound transmission efficiency than a liquid or gel couplant. "Shear-Wave Ultrasonic Inspection With a Dry Couplant", *NASA Tech Briefs*, Dec. 1994, pp. 77–78.

There is provided in accordance with the present invention an apparatus for ultrasound testing which does not require the use of an acoustic transmission gel, does not entail the usual drawbacks of a liquid couplant while in fact employing a liquid couplant, and does not have the drawbacks of a dry couplant material because a liquid couplant is employed.

BRIEF DESCRIPTION OF THE DRAWINGS

An understanding of additional aspects of the invention can be gained from a consideration of the following detailed description of representative embodiments thereof, in conjunction with the appended figures of the drawing, wherein:

FIG. 9 is a longitudinal cross-sectional view of the assembled ultrasound probe module of FIG. 8;

FIG. 10 is an end view of the assembled ultrasound probe module of FIG. 8;

FIG. 11 is a transverse cross-sectional view of the assembled ultrasound probe module of FIG. 8, taken along line 11—11 of FIG. 9;

FIG. 19 is a longitudinal cross-sectional view of the assembled ultrasound probe module of FIG. 18;

FIG. 20 is an end view of the assembled ultrasound probe module of FIG. 18;

FIG. 21 is a transverse cross-sectional view of the assembled ultrasound probe module of FIG. 18, taken along line 21—21 of FIG. 19;

FIG. 22 is an exploded view of an ultrasound probe module in accordance with a fourth embodiment of the present invention;

FIG. 23 is a longitudinal cross-sectional view of the assembled ultrasound probe module of FIG. 22;

FIG. 24 is an end view of the assembled ultrasound probe module of FIG. 22;

FIG. 25 is a transverse cross-sectional view of the assembled ultrasound probe module of FIG. 22, taken along line 25—25 of FIG. 23;

FIG. 26 is a fragmentary side elevation view, partially broken away, of the assembled ultrasound probe module; of FIG. 22;

DETAILED DESCRIPTION OF THE INVENTION

Figure 1:
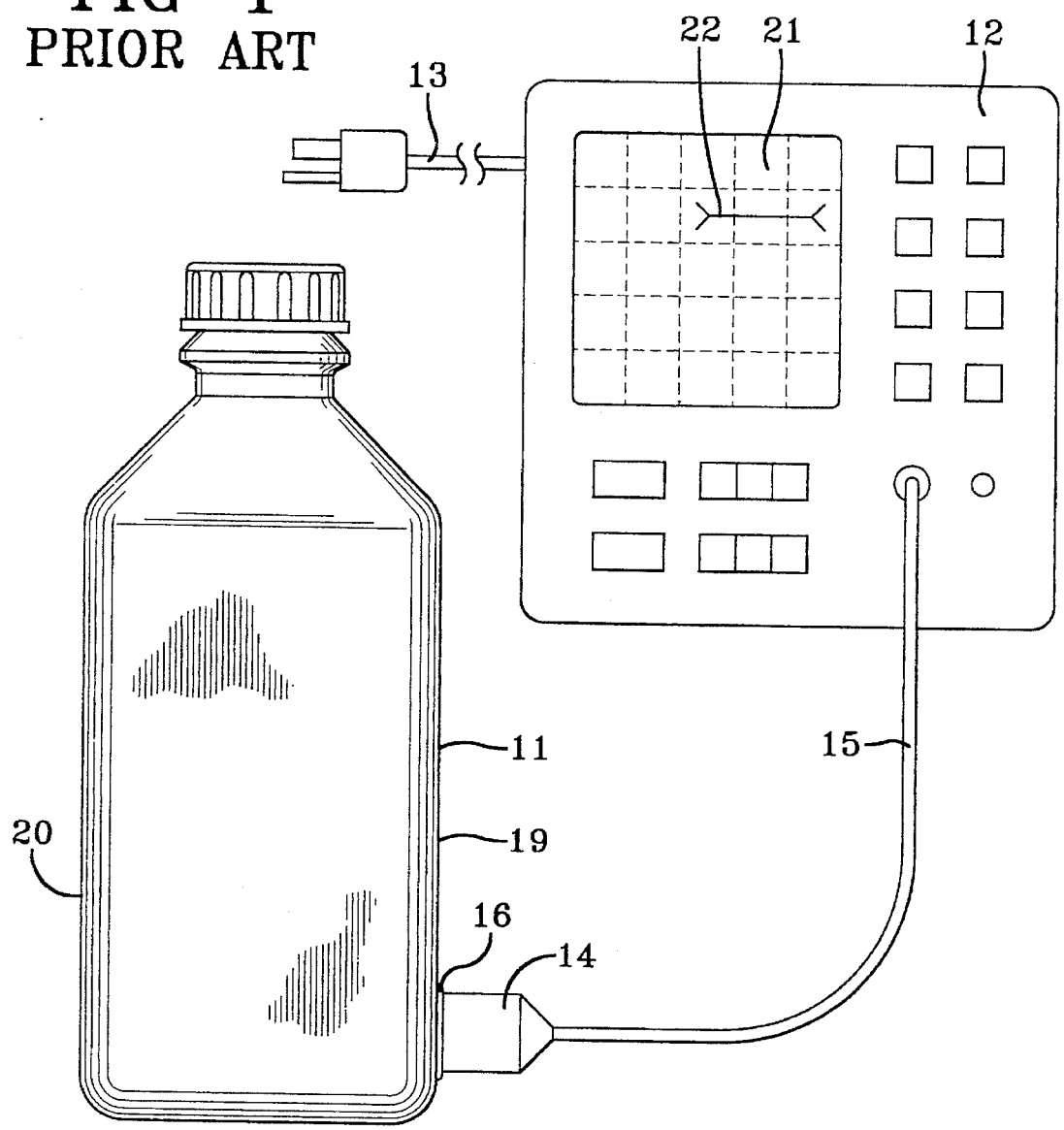
FIG. 1 is a representation of the use of ultrasound in testing for spoilage of a liquid nutritional product.
Figure 2:
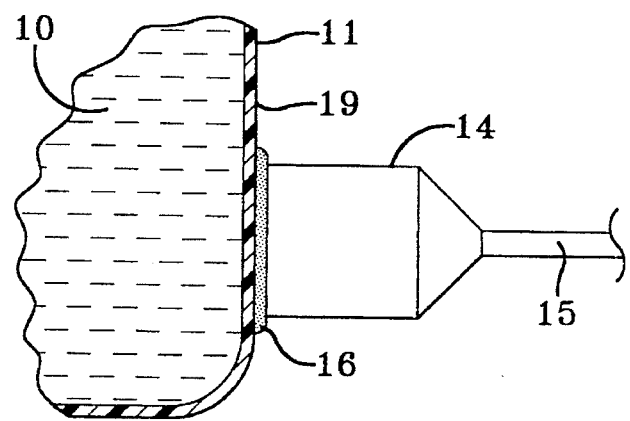
FIG. 2 is an enlarged fragmentary view, partially in section of the ultrasound testing process represented in FIG. 1.

Referring first to FIGS. 1 and 2, there is shown an example of a known practical use of ultrasound technology for evaluating the composition of a liquid 10 in a container 11 with respect to a selected physical characteristic. For example, if the liquid is a nutritional product it may be evaluated regarding spoilage which is manifested by a viscosity change or formation of particles or globules in the product matrix. An ultrasound operating system 12 is connectable to an external power source by a power cord 13 or has an internal power supply such as an alkaline battery. In this example, an ultrasound probe 14 which functions as both an ultrasound transducer and receiver communicates with the ultrasound operating system via a transmission cable 15. This type of system uses pulse-echo ultrasound technology. In accordance with widely accepted ultrasound testing techniques a coupling gel 16 which has acceptable acoustic wave transmission properties is applied to an exterior surface of a first wall 19 of the container, and thereafter the ultrasound probe 14 is brought into physical contact with the coupling gel.

A system operator, or a programmable controller, causes the ultrasound operating system 12 to generate, via the ultrasound transducer in the ultrasound probe 14, acoustical waves of a preselected amplitude, frequency, and intensity in a manner that is well known in the art. The acoustical waves are transmitted through the coupling gel 16 and the first wall 19 of the container, and thereafter pass through the liquid 10. If the acoustical waves encounter globules, bubbles, particulates or similar non-homogenous conditions in the liquid the acoustical waves can be disrupted and the acoustical energy dissipated or scattered about in the liquid matrix, such that no pulse echo or a minimal pulse echo is detected by the receiver located in the ultrasound probe 14. However, if the liquid 10 is sufficiently homogenous the acoustical waves will impinge upon an opposing second wall 20 of the container and be reflected back to the receiver disposed within the ultrasound probe 14. The ultrasound operating system 12 transforms the reflected acoustical waves into electronic signals which can be imaged on a screen 21 and/or transmitted to a controller and/or recorder (not shown). The amplitude of the reflected acoustical waves may be compared to a preselected standard 22 to evaluate a physical property of the liquid, such as viscosity, which may be an indicator of spoilage.

A disadvantage of this prior art ultrasound testing procedure is the expense, mess, and labor involved in applying the coupling gel 16 to the container prior to ultrasound testing, and thereafter removing the coupling gel from the container wall following the ultrasound testing.

Figure 3:
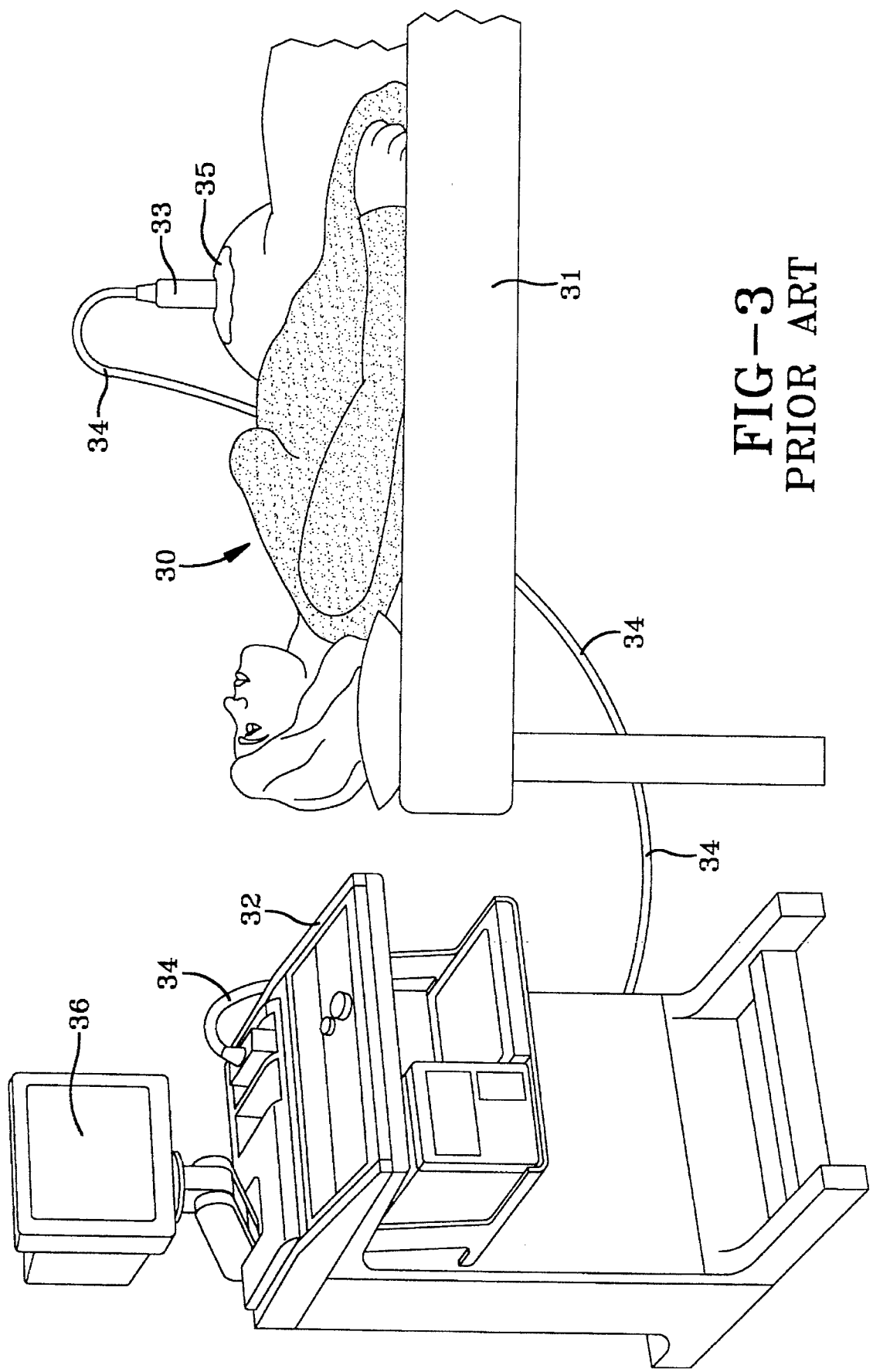
FIG. 3 is a pictorial representation of a medical application of ultrasound technology.

Referring next to FIG. 3 there is shown a well known medical application of ultrasound technology for evaluating the status of a fetus. A pregnant female 30 is shown reclining upon a supporting surface such as a table 31. An ultrasound operating system 32 suitable for this ultrasound imaging procedure, but operating substantially in the same basic manner described above with respect to FIGS. 1 and 2, communicates with an ultrasound probe 33 via a transmission cable 34. In this application of ultrasound technology the ultrasound probe 33 functions both as an ultrasound transducer and receiver. A suitable coupling gel 35 is applied to the skin of the expectant mother's abdomen in the region of the uterus. This necessitates the use of a significant quantity of coupling gel because, depending upon the stage of pregnancy, the abdomen may be quite large. An ultrasound technician places the ultrasound probe 33 on the abdomen of the patient in contact with the coupling gel and thereafter operates the ultrasound operating system 32 to cause acoustical waves of a preselected amplitude, frequency and intensity to be generated by the ultrasound transducer located in the ultrasound probe 33. The acoustical waves pass through the coupling gel, patient's skin, abdominal tissue, uterus wall and amniotic fluid to impinge upon the fetus/child and are thereafter reflected back through the same media to the receiver located in the ultrasound probe 33. The ultrasound operating system transforms the reflected acoustical waves into electronic signals which are projected on a screen 36 as an image of the fetus/child. The ultrasound operating system may also have the capability to print the image of the fetus/child onto a suitable media, usually paper, as a record of the results of the imaging procedure. The use of ultrasound technology to produce images of other anatomical features in the body of a person, or even an animal, are well known. Once again, a disadvantage of this prior art ultrasound imaging procedure is the expense, mess and labor involved in applying and removing the coupling gel.

Figure 4:
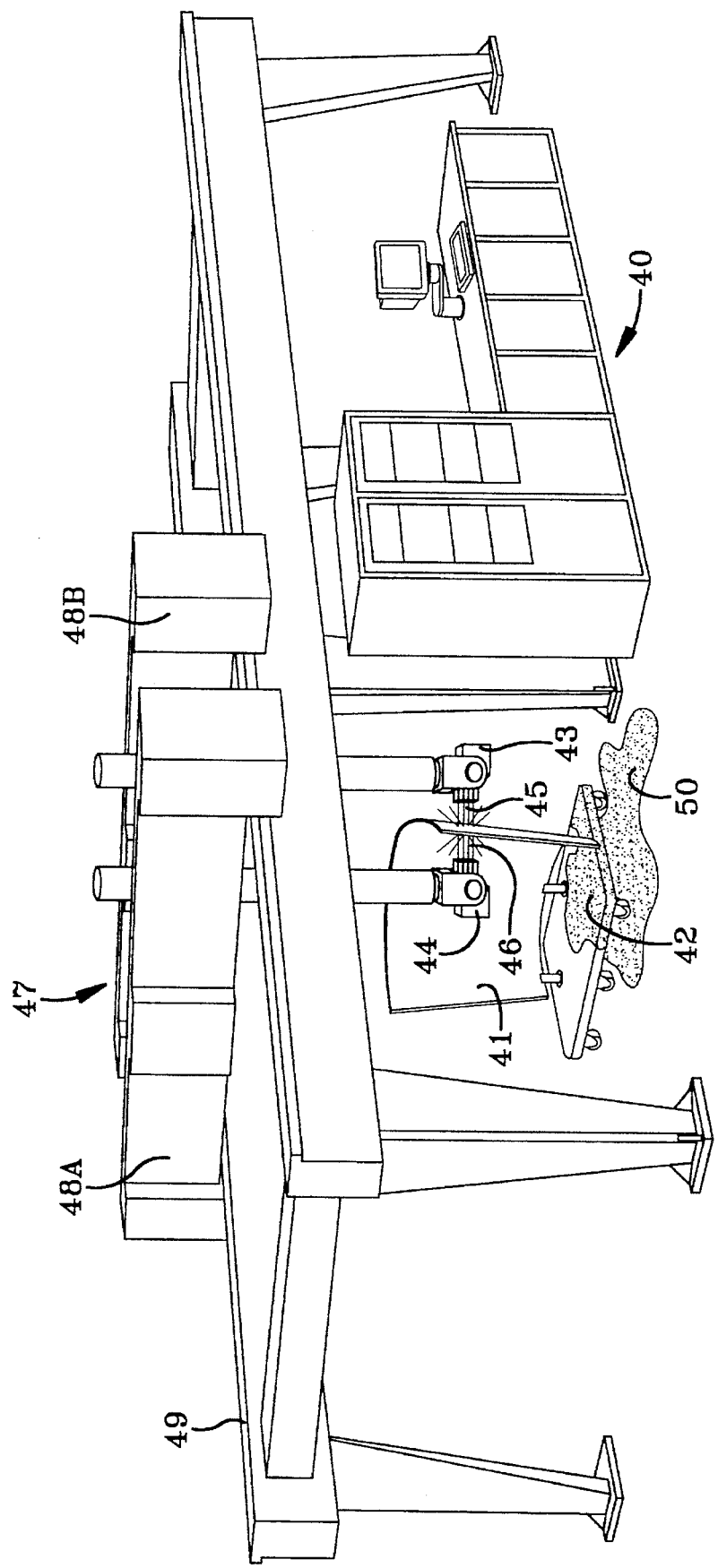
FIG. 4 is a pictorial representation of an industrial application of ultrasound technology.

Referring now to FIG. 4 there is shown an ultrasound operating system 40 adapted for use in evaluating the structural integrity of an object 41, such as a casting or forging. Depending upon the size and weight of the object being evaluated, it may be placed upon a suitable workpiece holding fixture 42, that may optionally have wheels as shown. In this application of ultrasound technology the ultrasound transducer is located in a first module 43 and the receiver is located in a second module 44. The two modules 43,44 are spaced apart such that the object 41 being evaluated may be disposed therebetween. Streams of water 45,46 are sprayed from the two modules 43,44 continuously to impinge upon the object 41 being evaluated. The streams of water function as couplants for transmission of the acoustical waves during the ultrasound testing procedure. Separate transmission cables (not shown) extend between the first and second modules 43,44 and the ultrasound operating system. A system operator, or suitable programmable controller, causes the ultrasound operating system to generate, via an ultrasound transducer located in the first module 43, acoustical waves of a preselected amplitude, frequency, and intensity. The acoustical waves are transmitted through the first stream of water 45, the object being evaluated 41, and the second stream of water 46 to a receiver located in the second module 44. Any feature in the object 41 being evaluated, such as a void or delamination, which impedes the uniform passage of the acoustical waves through the object will be detectable by the ultrasound operating system. This type of application of ultrasound technology is described, for example, in U.S. Pat. No. 4,726,231. A suitable manipulator system 47 may be employed for positioning the ultrasound transducer and receiving modules 43,44 with respect to the object being evaluated. For example, Panametrics, 221 Crescent Street, Waltham, Mass., U.S.A. distributes large scanning systems employing dual manipulator gantry systems which feature two synchronized 5-axis bridges 48A, 48B mounted on a gantry 49 for high speed contour ultrasound scanning of large objects.

The use of a stream of liquid, such as water, as an acoustical couplant is advantageous in a movable scanner type of ultrasound testing application because it eliminates the need for a coupling gel. The disadvantages of such a system are: the deflected liquid from the spray, which may need to be contained in some manner; the resultant runoff formed by deflected liquid which can result in a puddle; and/or the expense of a liquid collection and drainage system. Furthermore, the use of a liquid or gel acoustical coupler may be unacceptable in those instances where the object being evaluated is sensitive to moisture. An advantage of using a suitable liquid as an acoustical couplant is the excellent acoustical wave transmission qualities of such a media.

Figure 5:
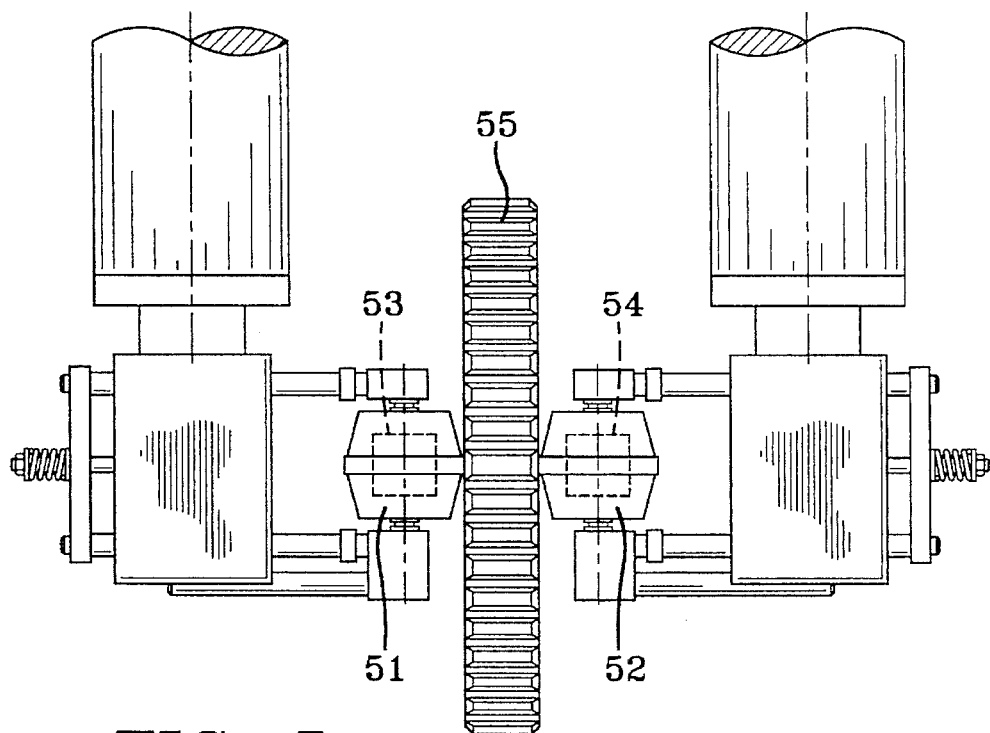
FIG. 5 is a pictorial representation of another industrial application of ultrasound technology.
Figure 6:
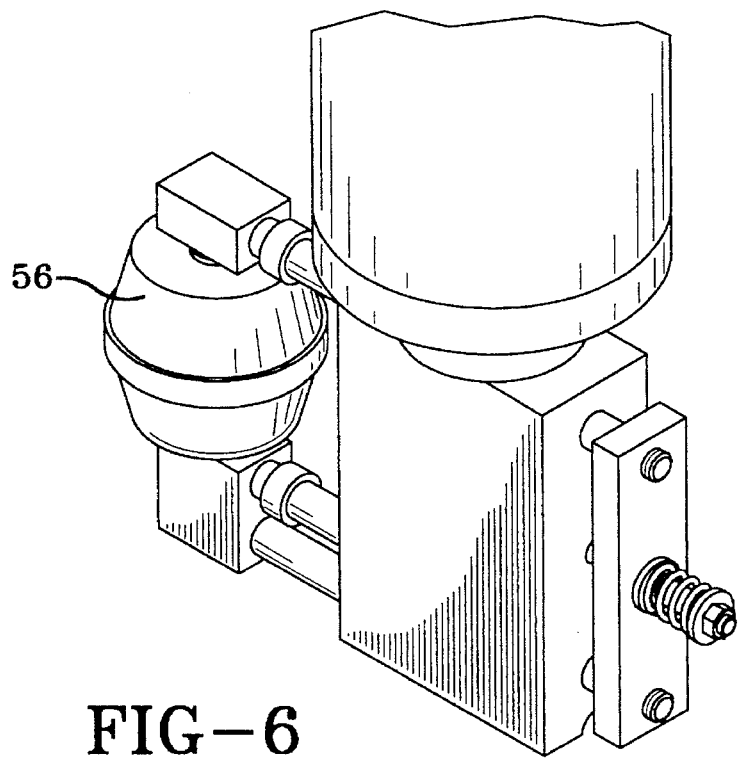
FIG. 6 is an enlarged fragmentary view, in perspective, of a roller type of ultrasound probe module.

Referring next to FIGS. 5 and 6 there are shown fragmentary views of an ultrasound imaging system of the type shown in FIG. 4 wherein the modules and associated streams of liquid have been replaced by first and second dry contact roller probes 51,52 comprising a solid material. FIG. 5 shows a test piece, in this case a gear 55, disposed between the dry contact roller probes 51,52 which can traverse the test piece while remaining aligned with one another.

A first dry contact roller probe 51 has an ultrasound transducer 53 disposed therein and a second dry contact roller probe has a receiver 54 disposed therein. The roller probes are coated with a solid material having relatively good ultrasound acoustic wave transmission properties, but not as good as those of liquids and coupling gels. Obviously, a single dry contact roller probe 56, as shown in FIG. 6, could have both an ultrasound transducer and a receiver disposed therein for use in appropriate ultrasound testing applications.

Figure 7:
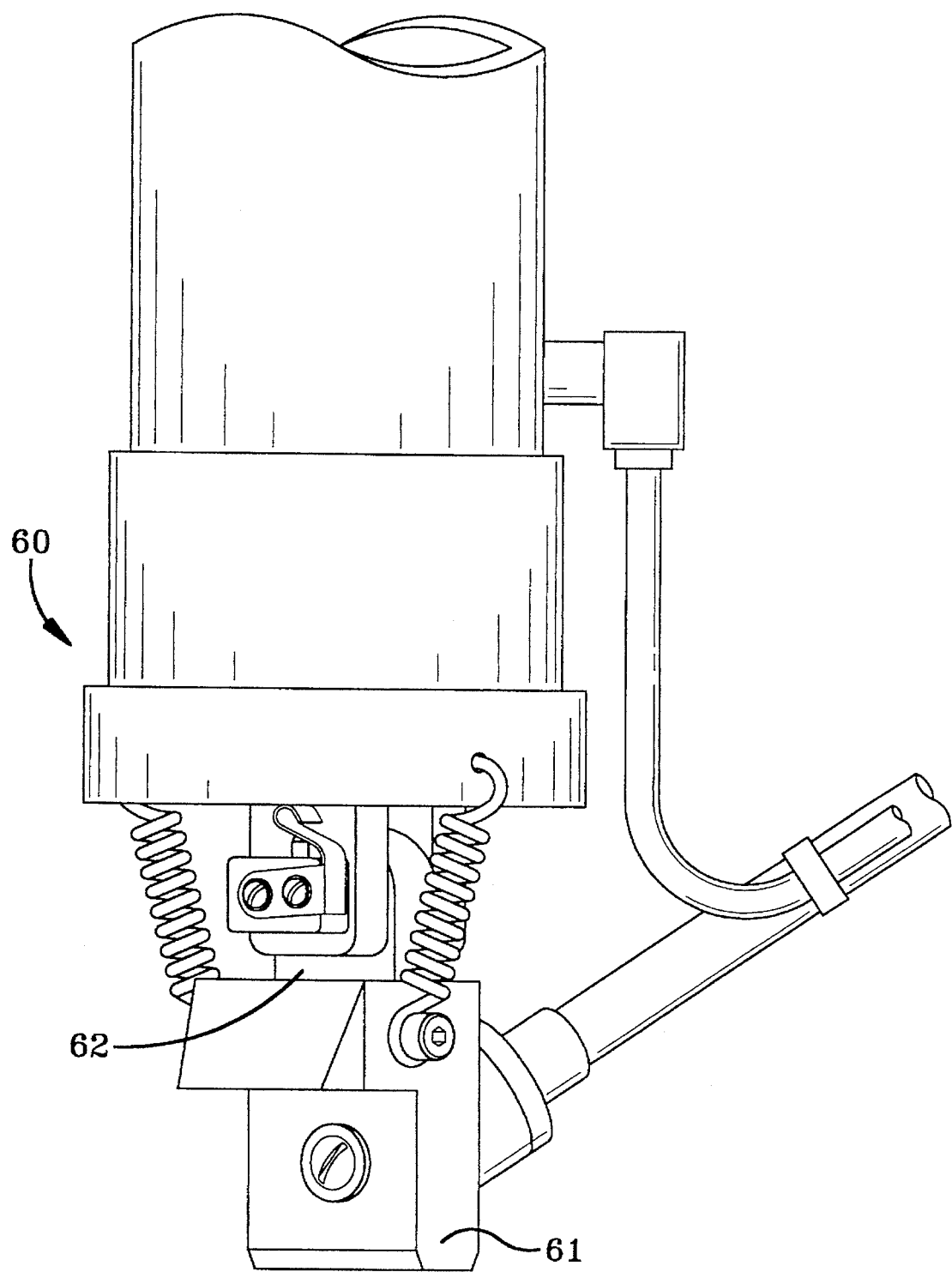
FIG. 7 is a pictorial representation of a prior art ultrasound testing device.

FIG. 7 is a fragmentary view of yet another embodiment of an ultrasound testing apparatus 60 wherein a dry contact acoustical couplant solid material 61 is used as an interface between an ultrasound transducer wedge (ultrasound probe) 62 containing both an ultrasound transducer and a receiver. As the ultrasound transducer wedge and couplant pad are pressed against a workpiece a surface of the compliant pad conforms to the surface of the workpiece, ensuring transfer of acoustic energy "with an efficiency lower than that of a liquid or gel couplant but nevertheless sufficient for the purpose." "Shear-Wave Ultrasonic Inspection With a Dry Couplant", *NASA Tech Briefs*, Dec. 1994 pp. 77–78. The ultrasound transducer wedge interacts with an ultrasound operating system (not shown) in the manner described above, for example with regards to FIGS. 1 and 2.

The ultrasound probe module of the present invention overcomes the disadvantages of using a gel or stream(s) of liquid as an acoustical couplant, and provides an acoustical couple that is at least as good as a couple formed by any currently identifiable solid acoustical couplant materials.

As used herein and in the claims an "ultrasound probe" refers to a device which is a transmitter (i.e. an ultrasound transducer) and/or a receiver for ultrasound waves. There are two well known, and widely used, types of ultrasound transducers. A "single type" transducer has a single ultrasound transducer and an "array type" transducer has a plurality of ultrasound transducers arranged either in a line or in a matrix. Both single type and array type ultrasound transducers may be used in the practice of the present invention.

As used herein and in the claims the term "membrane" is understood to have its' usual meaning as a thin pliable sheet or layer. The pliable feature of a membrane is important because it facilitates the conformity of the ultrasound probe module to the skin/surface of a person/object being evaluated or tested by ultrasound technology.

There is provided in accordance with the present invention a ultrasound probe module comprising an ultrasound probe; a porous membrane which cooperates with the ultrasound probe to define a chamber for containing a liquid ultrasound couplant, said chamber being located such that ultrasound waves traveling to or from the ultrasound probe travel through the chamber and porous membrane; and means for applying pressure to a liquid ultrasound couplant in said chamber to force the liquid ultrasound couplant through said porous membrane.

Figure 8:
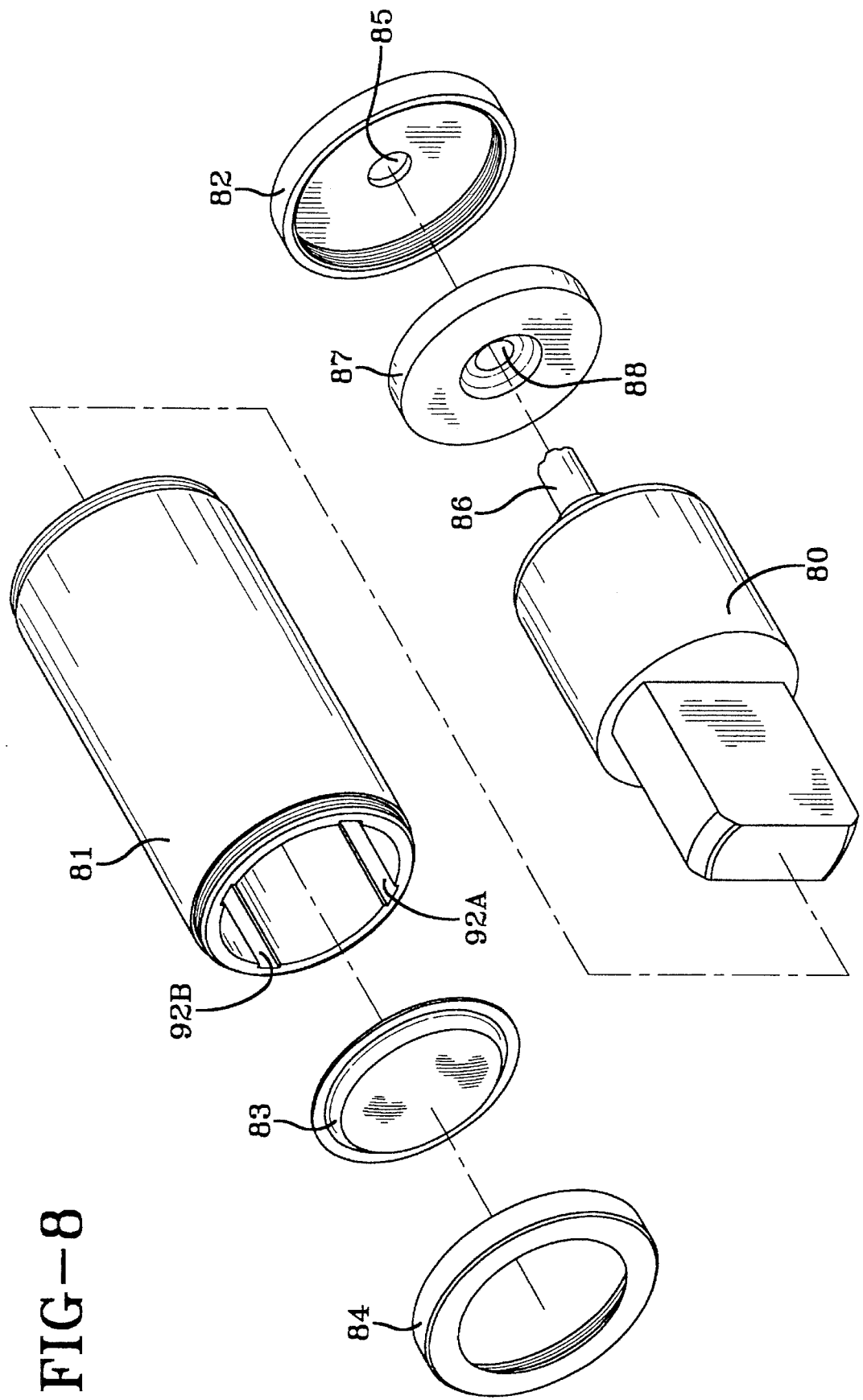
FIG. 8 is an exploded view of an ultrasound probe module in accordance with a first embodiment of the present invention.

An ultrasound probe module in accordance with a first embodiment of the present invention is shown in FIGS. 8–11 wherein: FIG. 8 is an exploded view of the ultrasound probe module; FIG. 9 is a longitudinal cross-sectional view of the ultrasound probe module; FIG. 10 is an end view of the ultrasound probe module; and FIG. 11 is a transverse cross-sectional view taken along line 11—11 of FIG. 9. An ultrasound probe 80 which functions as both an ultrasound transducer and receiver (of the type that may be used in a medical ultrasound imaging probe) is disposed within a housing. The ultrasound transducer employed in this first embodiment is an array type transducer. The housing in this embodiment is a tubular member 81 with an end cap 82. The housing for any of the embodiments disclosed herein may be made of any suitable material such as a metal or a polymer. A membrane 83 covers an opening in the housing and is secured to the housing by a retaining member such as a lock ring 84. In this embodiment both the end cap 82 and the lock ring 84 are threadably attached to the tubular member 81, but it is understood that other suitable means of attachment such as an interference fit, an adhesive, welding, chemical bonding and so forth may be employed for this purpose in any of the embodiments described herein. Furthermore, it will be evident to those skilled in the art that the tubular member and end cap may be integral. An aperture 85 in the end cap 82 facilitates passage of a transmission cable 86 therethrough. A sealing member, such as a gasket 87, is disposed intermediate of the ultrasound probe 80 and the end cap and has an aperture 88 therein which facilitates passage of the transmission cable 86 therethrough. The sealing member 87 impedes leakage of a liquid from the housing through the aperture 85 in the end cap or at the interface of the end cap and tubular member.

The porous membrane 83 is disposed with respect to the ultrasound probe 80 such that acoustical waves traveling to or away from the ultrasound probe 80 will pass through the porous membrane. The porous membrane has a pore size that will allow only a few molecules, preferably only one molecule, of a liquid acoustical couplant to pass therethrough when the liquid acoustical couplant is subjected to pressure. In a working example the porous membrane comprises a material having a pore size of about 0.2 μm, but a pore size as small as 0.01 μm may be employed in the practice of the invention. Pores of such sizes facilitate only dampness of the membrane or filling of capillary passageways in the membrane in the absence of a pressure differential. When an appropriate liquid acoustical couplant is subjected to a pressure of about 1 to 5 pounds per square inch (p.s.i.) the liquid acoustical couplant will pass through the porous membrane at such a slow rate that only a thin layer of moisture is formed on the surface of the porous membrane distal from the ultrasound probe. This thin layer of moisture may be so fine that it is difficult to feel while being sufficient moisture to serve as a very good acoustical coupling agent. Although it is understood that any suitable membrane material may be used in the practice of the present invention, an apparatus in accordance with the present invention has been manufactured using a polytetrafluoroethylene (PTFE) material distributed by Sartorius, G. N., of Göttinger, Germany through its U.S. affiliate Sartorius Filters Inc., 30940 San Clemente Street, Hayward, Calif., 94544, U.S.A. Sartorius' catalog number for the PTFE filters, used in reducing the present invention to practice is 118707.293 M. The specifications for this material per sales literature from Sartorius are presented in Table 1.

TABLE 1

| Pore size | 0.2 μm |
| --- | --- |
| Sterilizability | |
| Autoclaving | 121° C. or 134° C. |
| Dry Heat | 180° C. |
| Maximum temperature | 200° C. |
| Average flow rate per cm$^2$ for: | |
| Water, mL/min at Δp = 1 bar[1] | — |
| Isopropanol, mL/min at Δp = 1 bar[1] | 9–12 |
| Air, L/min at Δp = 0.05 bar[1] | 0.2 |
| Average pressure which is required to force air through an isopropanol wetted membrane filter | 1.2–1.6 bar |
| Average thickness | 65 μm |

[1]Δp = differential pressure

To the human eye this PTFE material appears to be thin with very smooth surfaces. Actually this material is very porous and is mostly air. This material is flexible, and has sufficient strength to withstand thousands of ultrasound test procedures unless torn or abraded. A material having a pore size of 0.2 μm has been used for porous filtration. Unlike a sponge this material has a rigid, pressure resistant structure and behaves like a tight-meshed multilayered sieve with uniform mesh holes, herein referred to as pores. This PTFE material is hydrophobic, therefore if water is to be used alone as a liquid acoustical couplant the porous membrane should be treated with (contacted by) isopropanol before the chamber in the ultrasound probe module is filled with water, and thereafter water should constantly be in contact with the porous membrane to keep it hydrophilic. A PTFE membrane may be treated with a solution of at least 50/50 isopropanol/distilled water, preferably 70/30 isopropanol/distilled water, by volume. Preferably the liquid acoustical couplant is a isopropanol/water solution with the preferable ratio of isopropanol to water being at least about 20/80, preferably about 50/50, by volume.

The low flow rate of a liquid acoustical couplant, in this example water and isopropanol, through a porous membrane at low differential pressures is an important feature of the present invention for reasons that will become apparent in the following discussion of the operation of an ultrasound probe module in accordance with the present invention.

As best shown in FIG. 9 a chamber 90 is disposed between the porous membrane 83 and the ultrasound probe 80. A liquid, such as the mixture of isopropanol and water described above, which has acceptable acoustical wave transmission properties may be introduced into the chamber 90. The liquid acoustical couplant is then subjected to pressure (in the working prototype about 1–5 p.s.i., but has been operated using only gravity feed), such that the liquid flows through the porous membrane at a low rate and wets the side of the porous membrane that is distal from the ultrasound probe 80. The porous membrane should comprise a material having acoustical wave transmission characteristics which are sufficiently similar to those of the liquid couplant such that the resultant ultrasound imaging will be of acceptable quality for a given application.

The ultrasound probe module of FIGS. 8–11 has a structure which facilitates the introduction of a liquid acoustical couplant into a second chamber 91 in the region of the closed end of the housing. The second chamber 91 is in fluid communication with the first chamber 90 via one or more channels 92A, 92B, 92C, 92D extending therebetween. As can be seen in FIG. 11, in this embodiment the channels are formed in the interior surface of tubular member 81, and are further defined by the exterior surface of the ultrasound probe 80. A liquid acoustical couplant under appropriate pressure is supplied to the ultrasound probe module through a conduit 93, which in this embodiment is integrated into the transmission cable 86, and fills the second chamber 91 through aperture 94. Conduit 93 extends to a reservoir (not shown) of a liquid acoustical couplant that is supplied under pressure by a pump, or compressed air, or any suitable means to the ultrasound probe module. The retaining ring may be loosened to facilitate bleeding air from the ultrasound probe module when the liquid acoustical couplant is introduced into the ultrasound probe module. Such a system is advantageous for a continuous operation type of ultrasound testing (e.g. containers on a conveyor) or when a large item (e.g. an aircraft component) is being tested. In this embodiment of the invention a liquid acoustical couplant is supplied to a chamber 90 disposed within the ultrasound probe module, at least a portion of the chamber 90 being linearly aligned with (a) an ultrasound probe and (b) a porous membrane 83, and thereafter passes through the porous membrane to wet a surface of the porous membrane which is distal from the ultrasound probe 80. When the porous membrane is placed in physical contact with, for example, a surface of an object, or skin of a person or animal, an acoustic couple is formed between the ultrasound probe and the object, person or animal which is to be evaluated by otherwise known ultrasound techniques. The need for costly, messy and labor intensive acoustical couplant gel is eliminated. The need for a spraying a continuous stream of acoustical couplant using sophisticated, costly equipment, and the resultant undesirable need for containing the run-off from this prior art technique is likewise eliminated.

An ultrasound probe module in accordance with the present invention has been successfully operated using both distilled water and an isopropanol/distilled water solution as a liquid acoustical couplant at a pressure of 1 to 5 p.s.i. However, alternative liquid acoustical couplant materials may be used with a PTFE membrane that has been treated with (exposed to) isopropanol as long as the liquid exhibits ultrasound transmission capability similar to water either with or without chemical (wet) treatments. The porous membrane can be made of any material having appropriate pore sizes and ultrasound transmission capability similar to water, either with or without chemical (wet) treatments.

In its broadest sense the present invention may employ a porous membrane of any material with suitable ultrasound transmission capability, that would allow a flowable substance with suitable ultrasound transmission capability, to be slowly forced through the pores in the membrane such that the surface of the membrane distal from the ultrasound probe is merely wetted at a slow constant rate. For example, if a stainless steel membrane is employed in an ultrasonic imagining module for testing aluminum castings, a grease such as that taught in U.S. Pat. No. 4,929,368 or even a low viscosity gel may be used as the liquid acoustical couplant.

An ultrasound test using an ultrasound probe module of the present invention may be conducted by: (a) providing an ultrasound probe module comprising (i) an ultrasound probe, (ii) a porous membrane which cooperates with the ultrasound probe to define a chamber, said chamber being located such that ultrasound waves traveling to or from the ultrasound probe will travel through the chamber and porous membrane; (b) introducing a liquid acoustical couplant into the chamber in said ultrasound probe module; (c) applying pressure to the liquid acoustical couplant which cause the liquid acoustical couplant to pass through the pores of said porous membrane; (d) placing the porous membrane against a surface; and (e) activating the ultrasound probe. It is understood that steps (c), (d) and (e) may be performed simultaneously or in any order. If an ultrasound test is to be conducted on an object having two opposing surfaces and it is desired to use two ultrasound probe modules, steps (a) through (e) are performed with regards to both opposing surfaces, step (e) being performed simultaneously with regards to both surfaces, one of said ultrasound probes functioning as an ultrasound transducer and the other ultrasound probe functioning as an ultrasound receiver.

Figure 12:
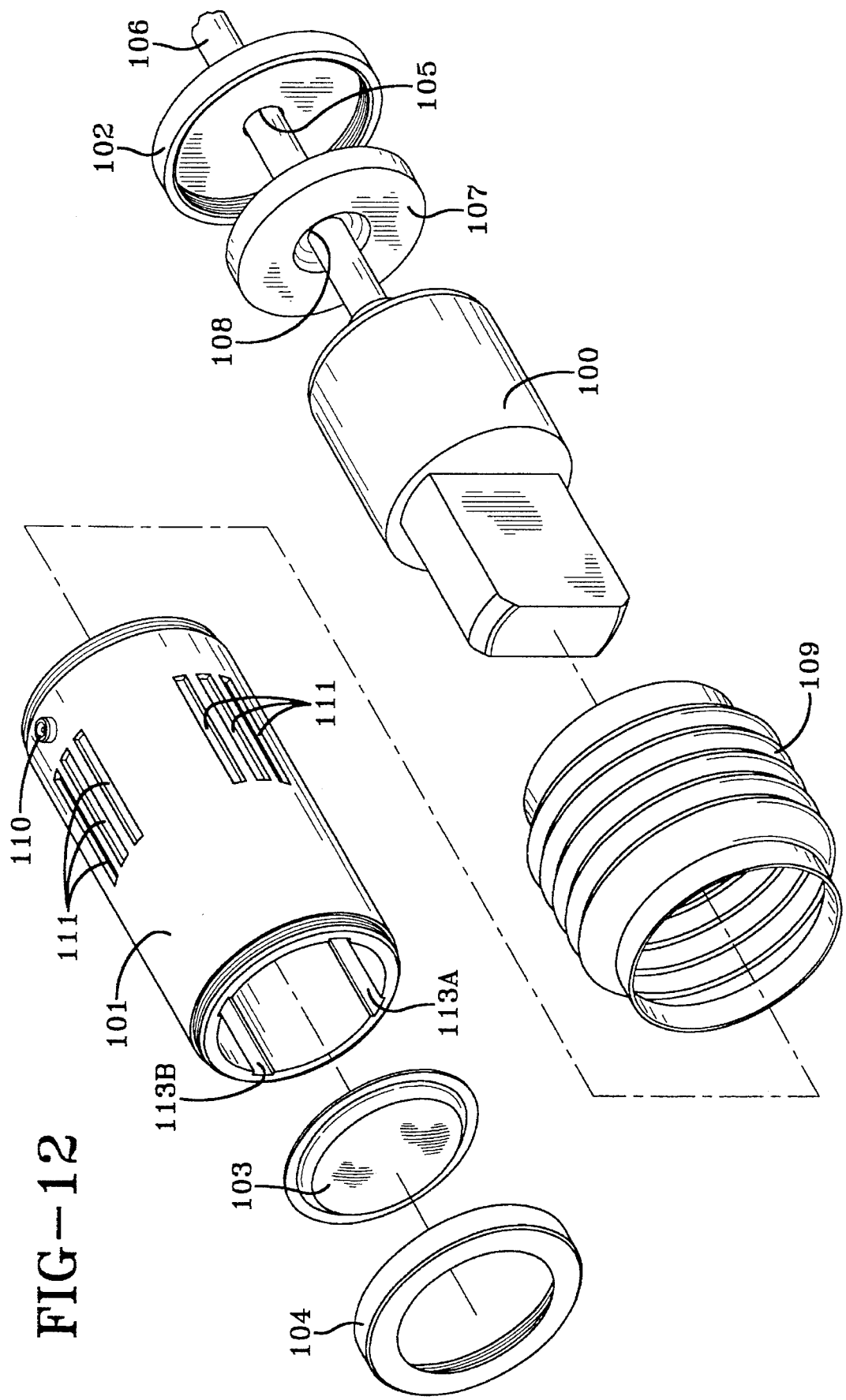
FIG. 12 is an exploded view of an ultrasound probe module in accordance with a second embodiment of the present invention.
Figure 13:
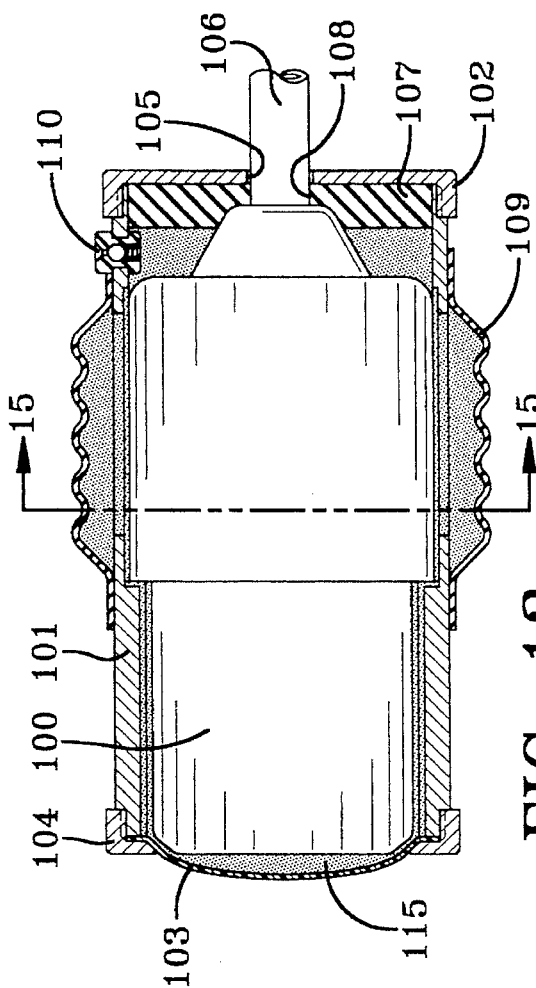
FIG. 13 is a longitudinal cross-sectional view of the assembled ultrasound probe module of FIG. 12.
Figure 14:
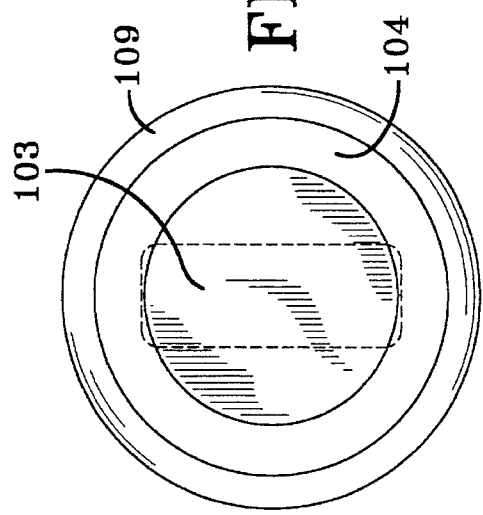
FIG. 14 is an end view of the assembled ultrasound probe module of FIG. 12.
Figure 15:
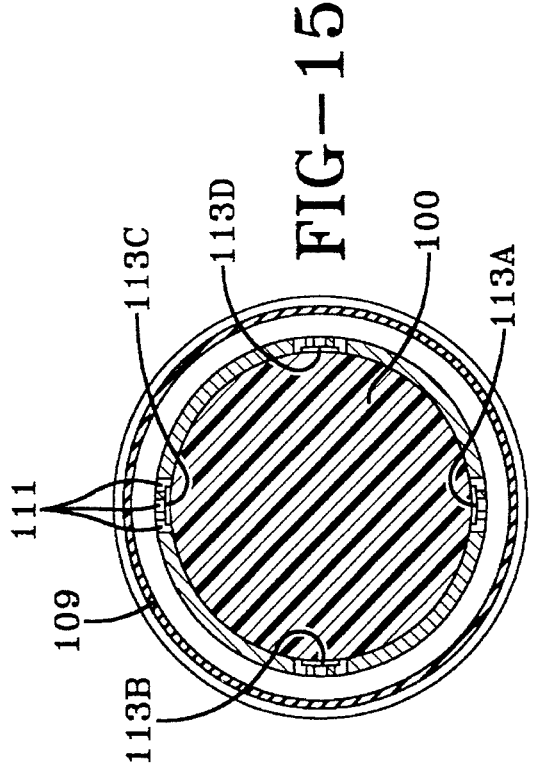
FIG. 15 is a transverse cross-sectional view of the assembled ultrasound probe module of FIG. 12, taken along line 15—15 of FIG. 13.
Figure 16:
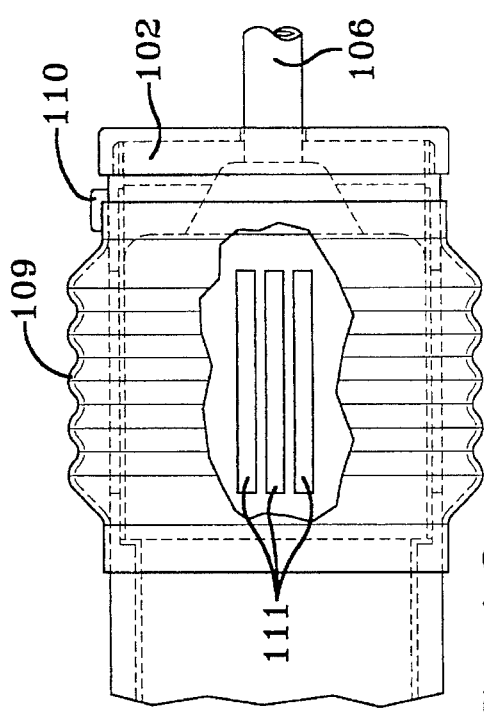
FIG. 16 is a fragmentary side elevation view, partially broken away, of the assembled ultrasound probe module of FIG. 12.
Figure 17:
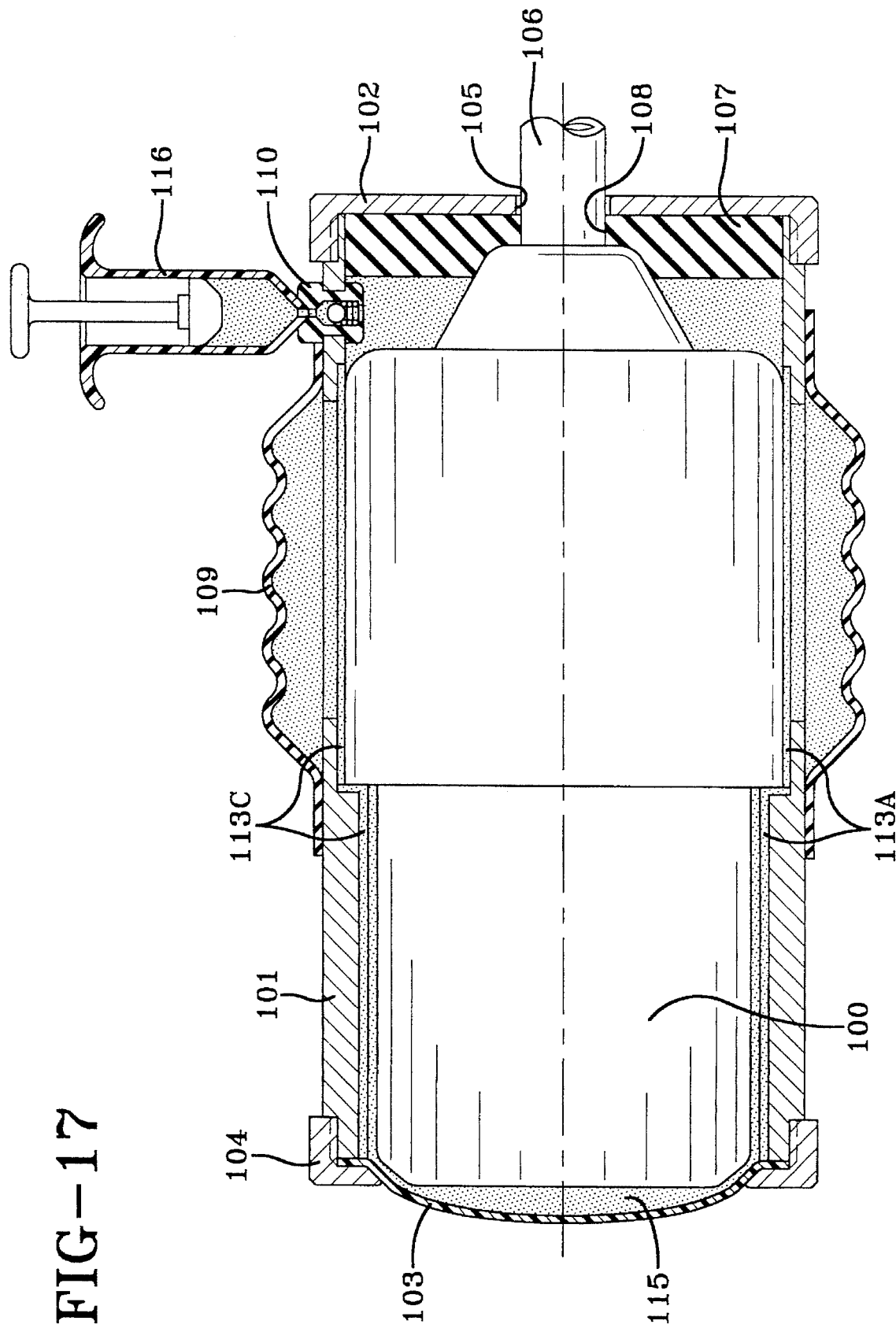
FIG. 17 is similar to FIG. 13 but illustrates a method of injecting a liquid acoustical couplant into the ultrasound probe module.

Referring next to FIGS. 12–17 there is shown a second embodiment of an ultrasound probe module in accordance with the present invention wherein: FIG. 12 is an exploded view thereof; FIG. 13 is a longitudinal cross-sectional view of the ultrasound probe module; FIG. 14 is an end view of the ultrasound probe module; FIG. 15 is a transverse cross-sectional view taken along line 15—15 of FIG. 13; FIG. 16 is a fragmentary side elevation view, partially broken away, of the ultrasound probe module; and FIG. 17 is similar to FIG. 13 but illustrates a method of injecting a liquid acoustical couplant into the ultrasound probe module. This second embodiment of the invention is similar to the first embodiment, described above, with the difference being that pressure is exerted upon the liquid acoustical couplant manually rather than by mechanical or electromechanical means.

An ultrasound probe 100, which is an array type ultrasound transducer, is disposed within a tubular housing 101 with an end cap 102. A porous membrane 103 covers an opening in the housing and is secured to the housing by a retaining member such as a lock ring 104. An aperture 105 in the end cap 102 facilitates passage of a transmission cable 106 therethrough. A sealing member such as gasket 107 is disposed between the ultrasound probe 100 and the end cap and has an aperture 108 therein which facilitates passage of the transmission cable 106 therethrough.

As in the first embodiment the porous membrane 103 is disposed with respect to the ultrasound probe such that acoustical waves traveling towards or away from the ultrasound probe 100 will pass through the porous membrane, which has the same properties described above with respect to the first embodiment. As in the first embodiment a chamber 115 is disposed between the porous membrane 103 and the ultrasound probe 100.

A flexible member 109, in this example of a generally cylindrical configuration with circumferential ribs, is located circumferentially about housing 101 and overlies at least one, preferably, as shown, a plurality of openings 111 in the housing 101. The flexible member may be formed of any suitably flexible material such as a plastic or rubber. The flexible member may be secured to the housing by an adhesive or a suitable retaining member. The liquid acoustical couplant, as described above, may be introduced into the housing via a one way valve 110. As shown in FIG. 17 the liquid acoustical couplant may be forced through the valve 110 using a syringe, but any other suitable means may be employed in place of the syringe. As described above with respect to the first embodiment the liquid acoustical couplant may flow through passageways 113A, 113B, 113C and 113D to reach the chamber 115 which is disposed between the ultrasound probe and the porous membrane.

A suitable amount of pressure, for instance 1–5 p.s.i., may be exerted upon the liquid acoustical couplant by gently squeezing on the flexible member, thereby forcing the liquid acoustical couplant to pass through the pores of the porous membrane 103, form a thin layer of moisture thereon, and create an acoustical couple with a person, animal, or object in the manner described above regarding the first embodiment. This second embodiment may be advantageous for use in medical or small scale industrial applications which do not warrant a more elaborate liquid supply/pressurization apparatus of the type employed in the first embodiment.

Figure 18:
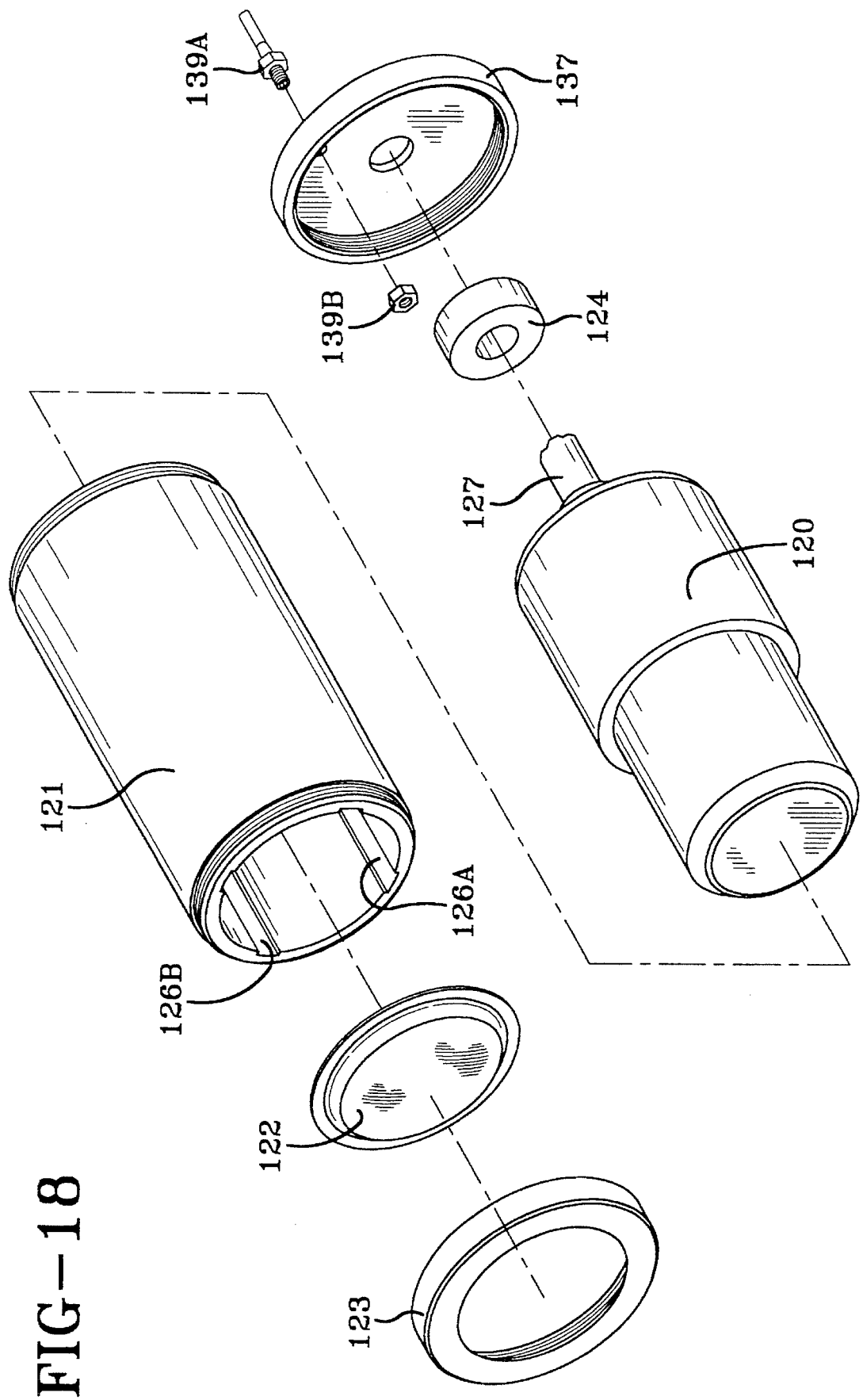
FIG. 18 is an exploded view of an ultrasound probe module in accordance with a third embodiment of the present invention.

Referring next to FIGS. 18–21 there is shown a third embodiment of an ultrasound probe module in accordance with the present invention wherein: FIG. 18 is an exploded view thereof; FIG. 19 is a longitudinal cross-sectional view of the ultrasound probe module; FIG. 20 is an end view of the ultrasound probe module; and FIG. 21 is a transverse cross-sectional view taken along line 21–21 of FIG. 19. This third embodiment is similar to the first embodiment described above with the difference being that the ultrasound probe employed is a single type ultrasound transducer and the supply line for the liquid acoustical couplant is not integral with the ultrasound transmission cable.

The ultrasound probe 120 is disposed within a tubular housing 121 with an end cap 137. A porous membrane 122 covers an opening in the housing and is secured to the housing by a retaining member such as lock ring 123. A transmission cable 127 for the ultrasound probe extends through apertures in the sealing member 124 and end cap 137, which are assembled together as described above with respect to the first two embodiments. A supply line 139A is secured to the end cap by retaining means 139B, such as a nut, and supplies a liquid acoustical couplant to the chamber 125 via passageways 126A, 126B, 126C and 126D in the manner described above with respect to the first embodiment. The ultrasound probe module of this third embodiment functions in the manner described above with regards to the first embodiment, except that the ultrasound probe is a single type ultrasound transducer.

Referring next to FIGS. 22–26 there is shown an ultrasound probe module in accordance with a fourth embodiment of the present invention wherein: FIG. 22 is an exploded view thereof; FIG. 23 is a longitudinal cross-sectional view of the ultrasound probe module; FIG. 24 is an end view of the ultrasound probe module; FIG. 25 is a transverse cross-sectional view taken along line 25—25 of FIG. 23; and FIG. 26 is a fragmentary side elevation view, partially broken away, of the ultrasound probe module. This fourth embodiment of the invention is similar to the other three embodiments, especially the second embodiment, but employs an ultrasound probe which is a single type ultrasound transducer and has the one way valve for introducing the liquid acoustical couplant into the module located in the end cap instead of the tubular housing.

The ultrasound probe 130 is disposed within a tubular housing 131 having at least one opening, and preferably a plurality of openings 135, extending through the wall of the housing. A transmission cable 127 for the ultrasound probe extends through apertures in a sealing member 127 and end cap 137 which are assembled with the housing in a manner that has been described above for the first three embodiments. A porous membrane 132, as described above, is secured to the housing by a retaining member, such as a lock ring 133. The one way valve 136 assembled with an end cap 137 facilitates the introduction of a liquid acoustical couplant into the ultrasound probe module in the manner described above regarding the second embodiment. A flexible member 34 of the type described above for the second embodiment is assembled with the housing to enclose the openings 135 through the housing. In all respects other than that the ultrasound probe 130 is a single type ultrasound transducer the fourth embodiment functions as substantially the same as the embodiment shown in FIGS. 12–17 to force a liquid couplant along passageways 149A, 149B, 149C and 149D to a chamber 138 and through the porous membrane 132 to form an acoustical couple between the ultrasound probe and the surface of an object, or skin of a person or animal being subjected to ultrasound testing.

Figure 27:
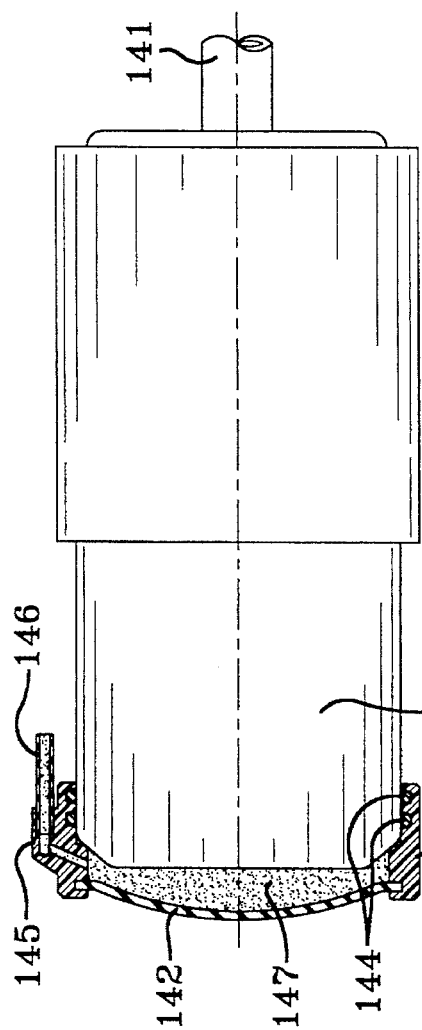
FIG. 27 is a side view, partially in section, of an ultrasound probe module in accordance with a fifth embodiment of the invention.
Figure 28:
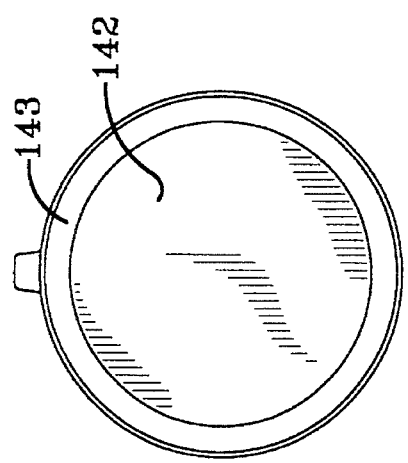
FIG. 28 is an end view of the embodiment shown in FIG. 27.

Referring next to FIGS. 27 and 28 there is shown a side view, partially in section, and an end view of an ultrasound probe module in accordance with a fifth embodiment of the present invention. It is understood that the ultrasound probe 140 may be either a single type or array type ultrasound transducer, or a receiver, or a combination transducer and receiver. A porous membrane 142, of the type described above, is assembled with a retaining member 143, here a retaining ring, which is attached directly to the ultrasound probe 140. In this example the retaining ring is threadably attached to the ultrasound probe as shown at 144. The ultrasound probe, retaining member, and porous membrane cooperate with one another to form a chamber 147 which is aligned with both the porous membrane and the ultrasound probe. A suitable liquid acoustical couplant, of the type described above, is introduced into the chamber 147 via a supply tube 146 and aperture through the retaining ring. The supply tube may extend to a reservoir of a liquid acoustical couplant (not shown) which is supplied under pressure as described above with respect to the first embodiment. The ultrasound probe 140 communicates with an ultrasound operating system (not shown) via a transmission cable 141. The pressurized liquid acoustical couplant is forced through the porous membrane 142 to form an acoustical couple between the ultrasound probe and the surface of an object, or skin of a person or animal being subjected to ultrasound testing in the manner described above.

Figure 29:
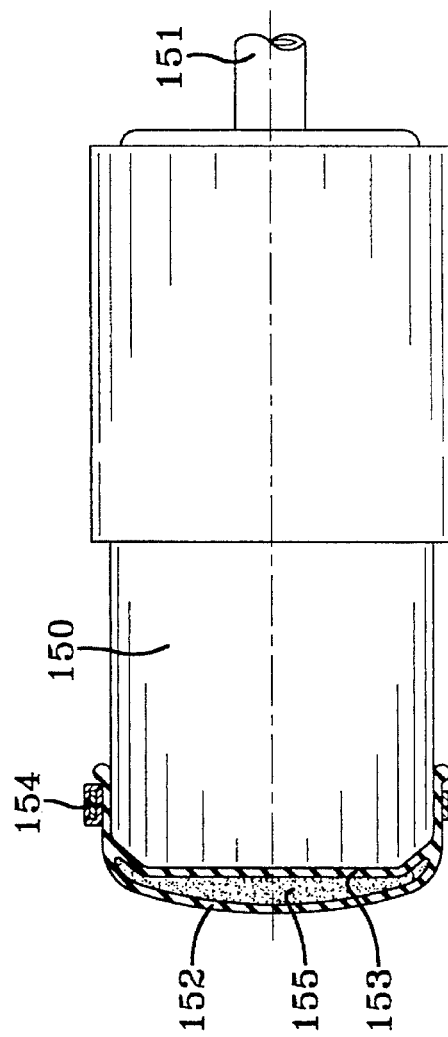
FIG. 29 is a side view, partially in section, of an ultrasound probe module in accordance with a sixth embodiment of the invention.
Figure 30:
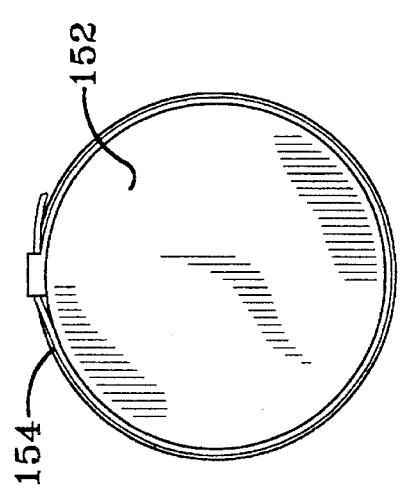
FIG. 30 is an end view of the embodiment shown in FIG. 29.

Referring next to FIGS. 29 and 30 there is shown a side view, partially in section, and an end view of an ultrasound probe module in accordance with a sixth embodiment of the invention. It is understood that the ultrasound probe 150 may be either a single type or array type ultrasound transducer, or a receiver, or a combination transducer and receiver. The ultrasound probe 150 communicates with an ultrasound operating system (not shown) via a transmission cable 151.

A disposable cartridge having one wall 152 formed of a porous membrane material, for example the PTFE described above, is secured to the ultrasound probe by retaining means 154 such as a plastic tie, an "O" ring cooperating with a groove (not shown) in the ultrasound probe, or any suitable retaining means. The other wall 153 of the cartridge is also a membrane, but does not need to be porous. As used herein and in the claims the term "cartridge" is understood to have its usual meaning of a case or container that holds a substance or material which is difficult, troublesome or awkward to handle, and that can be easily changed. A chamber 155 is defined by the cartridge walls 152 and 153. The chamber 155 is pre-filled with a suitable liquid acoustical couplant of the types described above. This disposable cartridge has particular application in performing medical ultrasound testing because a new cartridge may be employed for each patient by placing the porous membrane 152 against the skin of a patient, or surface of an object, and manually exerting pressure against the cartridge by pushing on the ultrasound probe the ultrasound operator may force the liquid couplant through the porous membrane and form an acoustical couple between the ultrasound probe and the skin of a patient, or surface of an object being used.

There is provided in accordance with the invention an assembly comprising: (a) an ultrasound probe; and (b) a cartridge attached to the ultrasound probe comprising a porous membrane connected to a second membrane to form a chamber containing a liquid acoustical couplant which will pass through the porous membrane when subjected to pressure, the cartridge being attached to the ultrasound probe such that ultrasound waves traveling to or away from the ultrasound probe will pass through said chamber and porous membrane and that when the porous membrane is placed against the surface of an object or animal pressure may be exerted upon the liquid acoustical couplant by pushing on the ultrasound probe. An ultrasound test using this sixth embodiment may be conducted by: (a) providing an assembly comprising: (i) an ultrasound probe and (ii) a cartridge attached to the ultrasound probe comprising a porous membrane attached to a second membrane to form a chamber containing a liquid acoustical couplant, the cartridge being attached to the ultrasound probe such that ultrasound waves traveling to or away from the ultrasound probe will pass through said chamber and porous membrane; (b) placing the porous membrane against a surface; (c) pressing on the ultrasound probe to force the liquid acoustical coldplant to pass through the porous membrane; and (d) activating the ultrasound probe. Steps (c) and (d) can be performed simultaneously or in any order.

Figure 31:
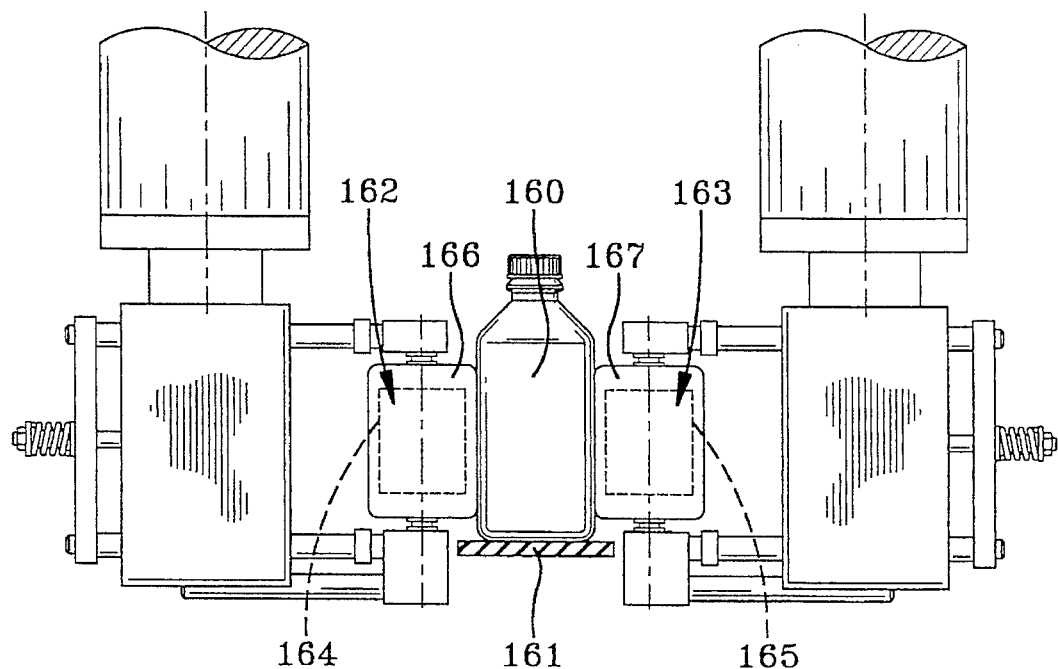
FIG. 31 is a pictorial representation of a pair of ultrasound probe modules in accordance with a seventh embodiment of the invention being used to evaluate the contents of a container.
Figure 32:
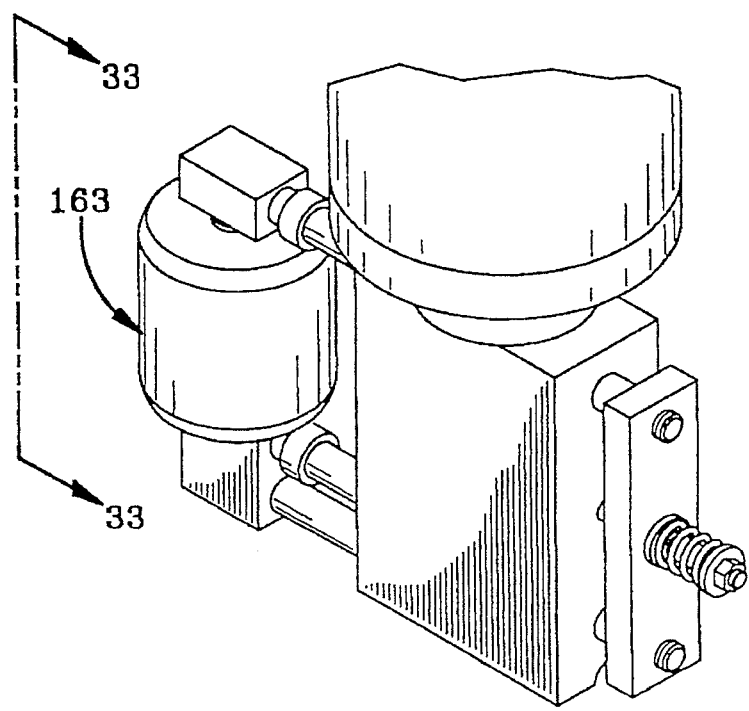
FIG. 32 is an enlarged fragmentary view, in perspective, of the embodiment shown in FIG. 31.
Figure 33:
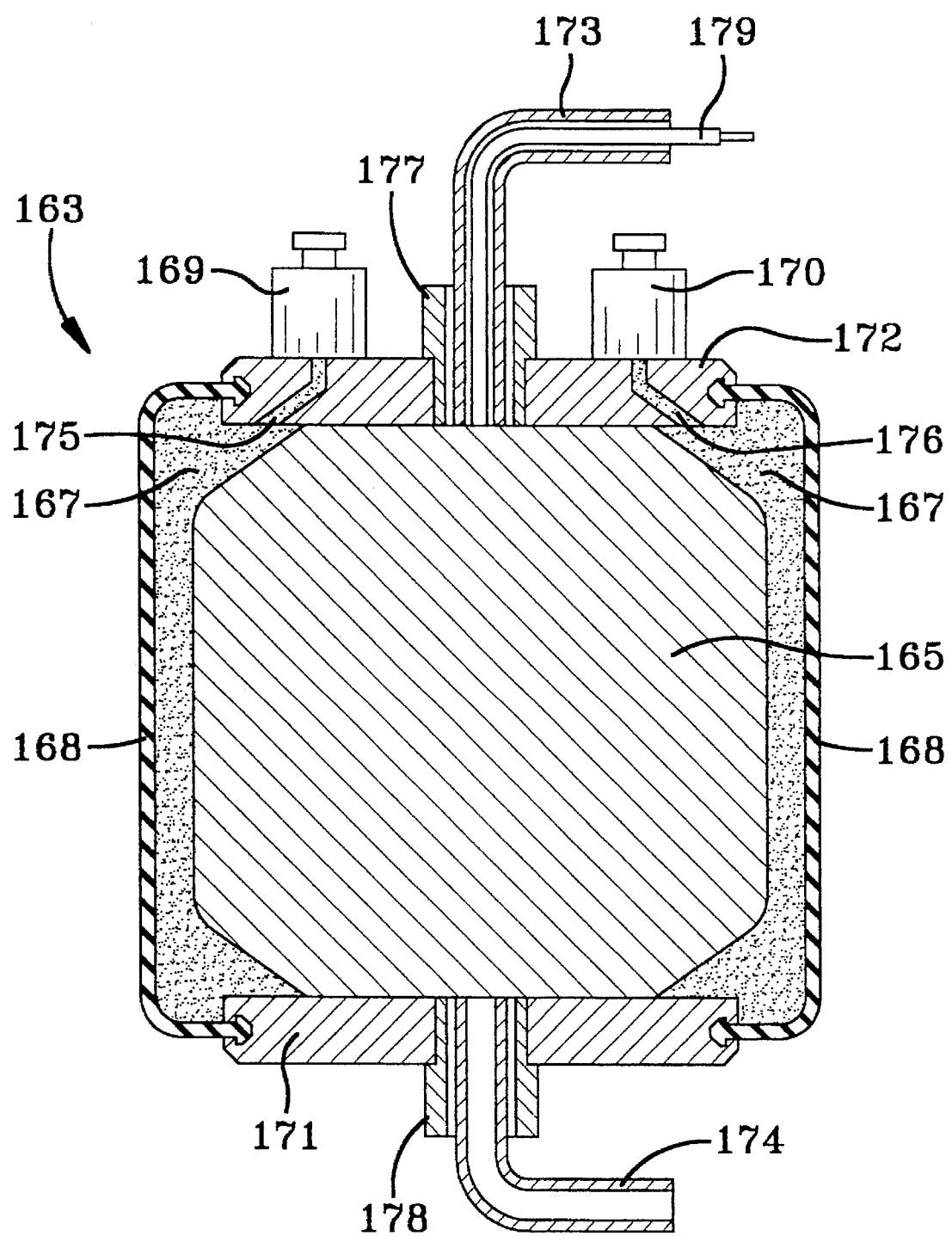
FIG. 33 is a fragmentary cross-section of the embodiment shown in FIG. 31 taken along line 33—33 in FIG. 32.

Referring next to FIGS. 31–33 there is shown a seventh embodiment of the invention wherein: FIG. 31 shows a pair of ultrasound probe modules being used to evaluate the contents of a container; FIG. 32 is an enlarged fragmentary perspective view, of one of the ultrasound probe modules; and FIG. 33 is a fragmentary cross-section of an ultrasound probe module taken along line 33—33 of FIG. 32. A container 160 traveling down a conveyor belt 161 passes between two roller ultrasound probe modules 162, 163. Each of the roller ultrasound probe modules 162, 163, has an ultrasound probe 164, 165 circumferentially surrounded by a porous membrane 168 of the type described above for the other embodiments. A chamber 166, 167 extends circumferentially about the ultrasound probe and is supplied with a suitable liquid acoustical couplant through an inlet valve 169 and associated passageway 175 which may be connected to a reservoir of liquid acoustical couplant (not shown) via a supply line (not shown). A bleeder valve/relief valve 170 communicates with the chamber 167 via a passageway 176. End housings 171,172 are rotatably mounted on spindles 173, 174 using, for example, bushings 177, 178 and have the cylindrically configured porous membrane 168 attached thereto by any suitable means including lock rings, "O" rings, elastic members, and so forth. The ultrasound probe 165 communicates with an ultrasound operating system (not shown) via a transmission cable 179. The ultrasound probe may be only an ultrasound transducer or receiver, with the probes maintained in alignment as shown in FIG. 31, or the ultrasound probe may be both an ultrasound transducer and receiver in which case only a single roller ultrasound probe module would be needed. An apparatus of the type shown in FIG. 31 may be employed for high speed ultrasound testing of a plurality of objects, or the conveyor belt may be replaced by a fixture allowing a single large object to be evaluated in the manner illustrated in FIG. 5.

Figure 34:
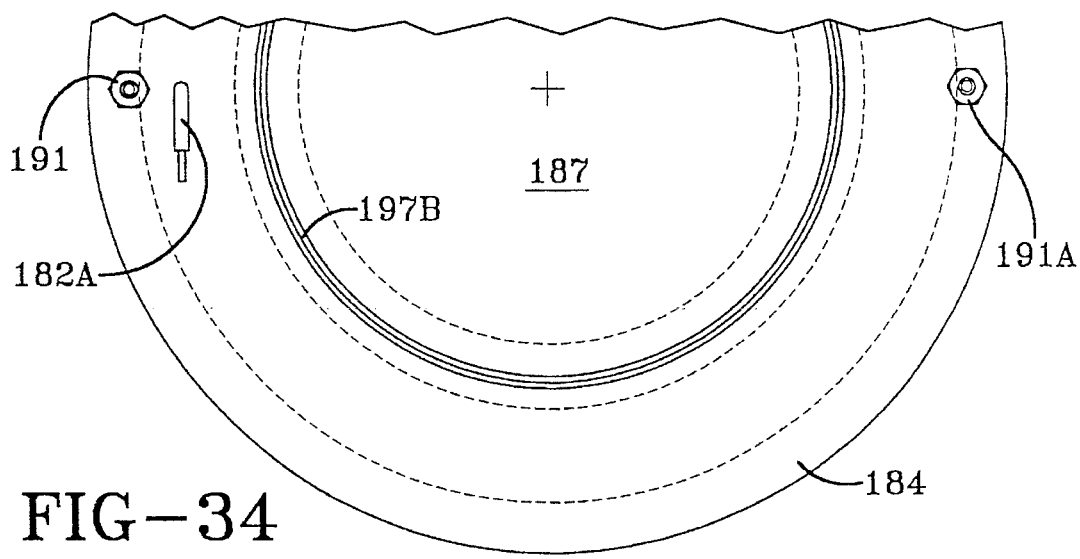
FIGS. 34 and 35 are a fragmentary top and a cross-sectional view, respectively, of a pair of ultrasound probe modules in accordance with an eighth embodiment of the invention being used to evaluate the integrity of the seal of a lid with the rim of a cup.
Figure 35:
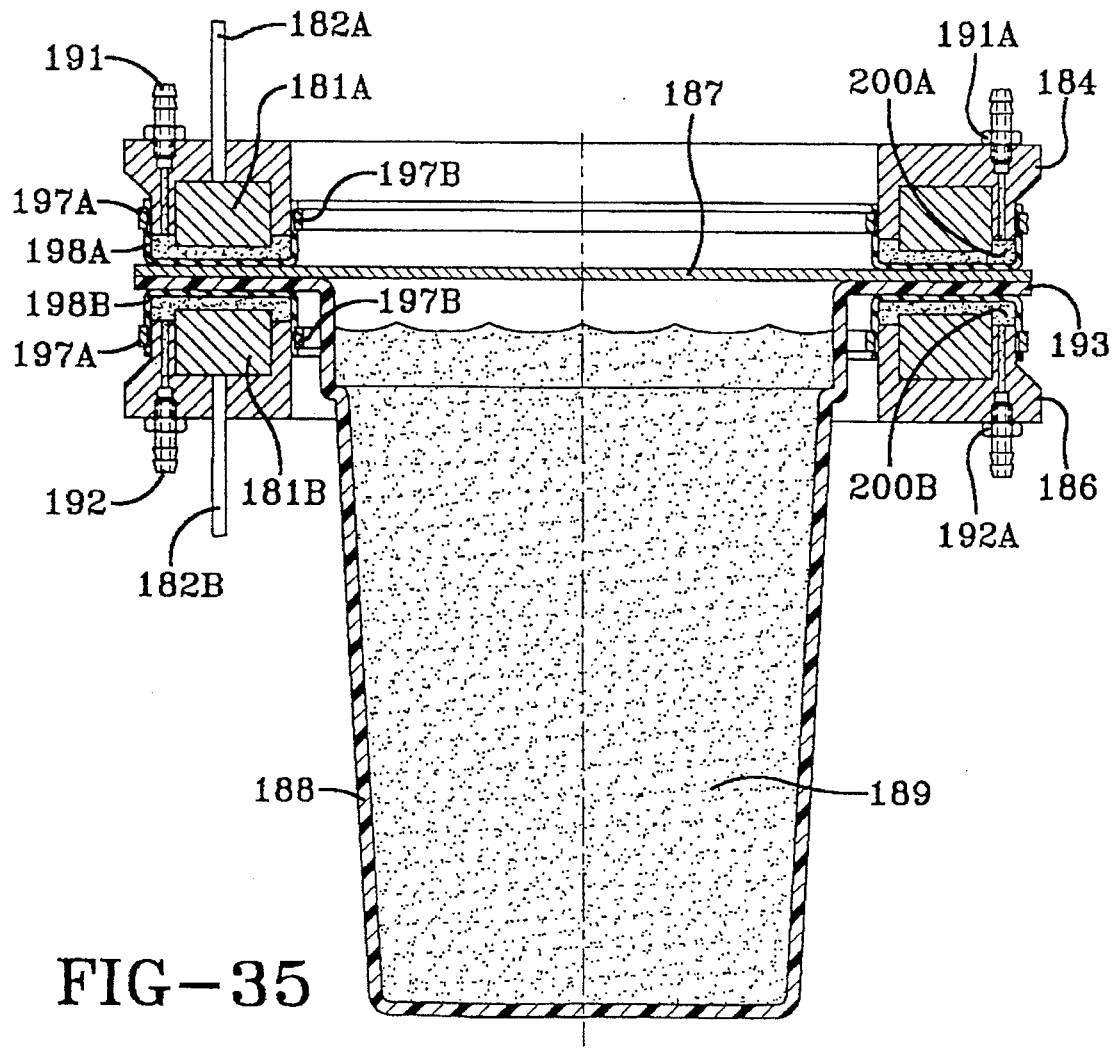

Referring next to FIGS. 34 and 35 there is shown a fragmentary top view and a cross-sectional view, respectively of a pair of ultrasound probe modules in accordance with an eighth embodiment of the invention being used to evaluate the integrity of the seal of a lid with the rim of a cup. A plastic cup 188 containing a nutritional product 189 has a lid 187 of a sheet of an appropriate material affixed to the rim 193 of the cup by appropriate means such as an adhesive or a heat sealing procedure. It is desirable to insure that the interface between the lid and the rim is free of voids which might allow contamination to enter the cup. Ultrasound probes 181A, 181B in the form of rings may be used in making such a seal integrity evaluation by incorporating them into ultrasound probe modules in accordance with the present invention.

Each of the ultrasound probes 181A, 181B communicates with an ultrasound testing system (not shown) via a transmission cable 182A, 182B. The ultrasound probes are each secured in a ring housing 184, 186, for example by molding a plastic housing around the ultrasound probe. Porous membranes 198A, 198B are affixed to the housings by suitable means of attachment 197A, 197B such as lock rings, tension members or an adhesive, such that chambers 200A, 200B are disposed between the ultrasound probes and porous membranes in the manner described above. A liquid acoustical couplant is supplied to the chambers via inlet passages 191, 192 which are connected to reservoirs and pressurization means (not shown) in manners described above with regards to the first, third and fifth embodiments. Bleeder/pressure relief valves 191A, 192A function to bleed air from the chambers and relieve excessive pressure. In the embodiment shown one of the ultrasound probes will be only an ultrasound transducer and the other only a receiver. This embodiment illustrates the versatility of the present invention to use specially configured ultrasound probes for testing objects of virtually any shape.

It is known in the ultrasound art to generate ultrasonic waves in an object by striking the object with a laser beam. An ultrasound probe module of the present invention in which the ultrasound probe is only a receiver could be in contact with one surface of an object when an opposing surface of the object is struck by a laser beam to generate an ultrasound wave.

While certain representative embodiments and details have been described for the purpose of illustrating the invention, it will be apparent to those skilled in the art that various changes and modifications may be made therein without departing from the spirit or scope of the invention.

We claim:

1. An ultrasound probe module comprising:

(a) an ultrasound probe;

(b) a porous membrane which cooperates with the ultrasound probe to define a chamber for containing a liquid ultrasound couplant, said chamber being located such that ultrasound waves traveling to or from the ultrasound probe travel through the chamber and porous membrane, said membrane being flexible and comprising a material having acoustical wave transmission characteristics which are similar to those of a liquid couplant which is passable therethrough and said membrane having a rigid pressure resistant structure so as to behave like a tight-meshed multi-layered sieve; and (c) means for applying pressure to a liquid ultrasound couplant in said chamber to force the liquid ultrasound couplant through said porous membrane.

2. An ultrasound probe module according to claim 1 wherein the porous membrane has pores therein of a size substantially equal to the size of a water molecule.

3. An ultrasound probe module according to claim 1 wherein the porous membrane has pores therein with a pore size in the range of about 0.01 μm to 0.2 μm.

4. An ultrasound probe module according to claim 1 wherein the porous membrane comprises polytetrafluoroethylene and has pores therein with a pore size in the range of about 0.01 μm to 0.2 μm.

5. An ultrasound probe module according to any one of claims 1–4 further comprising a housing which contains the ultrasound probe with the porous membrane being attached to the housing.

6. An ultrasound probe module according to any one of claims 1–4 wherein the porous membrane is attached directly to the ultrasound probe.

7. An ultrasound probe module according to any one of claims 1–4 further comprising a conduit which communicates with said chamber and is connectable to a reservoir of liquid acoustical couplant and pressure is applied to the acoustical couplant by a pump.

8. An ultrasound probe module according to any one of claims 1–4 further comprising a conduit which communicates with said chamber and is connectable to a reservoir of liquid acoustical couplant and pressure is applied to the acoustical couplant by compressed air.

9. An ultrasound probe module according to any one of claims 1–4 wherein pressure may be applied to the liquid acoustical couplant by manual means.

10. An ultrasound probe module according to any one of claims 1–4 wherein the ultrasound probe is a single type ultrasound transducer.

11. An ultrasound probe module according to any one of claims 1–4 wherein the ultrasound probe is an array type ultrasound transducer.

12. An ultrasound probe module according to any one of claims 1–4 wherein the porous membrane has a cylindrical configuration such that the porous membrane circumferentially surrounds the ultrasound probe and the ultrasound probe module is rotatable about an axis.

13. An ultrasound probe module according to any one of claims 1–4 wherein the ultrasound probe and porous membrane have a ring configuration.

14. An assembly comprising:

(a) an ultrasound probe; and (b) a cartridge attached to the ultrasound probe comprising a porous membrane connected to a second membrane to form a chamber containing a liquid acoustical couplant which will pass through the porous membrane when subjected to pressure, the cartridge being attached to the ultrasound probe such that ultrasound waves traveling to or away from the ultrasound probe will pass through said chamber and porous membrane and that when the porous membrane is placed against the surface of an object or animal pressure may be exerted upon the liquid acoustical couplant by pushing on the ultrasound probe.

15. An assembly according to claim 14 wherein said porous membrane is flexible and comprises a material having acoustical wave transmission characteristics which are similar to those of a liquid couplant which is passable therethrough and said membrane having a rigid pressure resistant structure so as to behave like a tight-meshed multi-layered sieve.

16. A method of performing an ultrasound test comprising the steps of:

(a) providing an ultrasound probe module comprising (i) an ultrasound probe, and (ii) a porous membrane, said membrane being flexible and comprising a material having acoustical wave transmission characteristics which are similar to those of a liquid couplant which is passable therethrough and said membrane having a rigid pressure resistant structure so as to behave like a tight-meshed multi-layered sieve, the porous membrane cooperating with the ultrasound probe to define a chamber, said chamber being located such that ultrasound waves traveling to or from the ultrasound probe will travel through the chamber and porous membrane;

(b) introducing a liquid acoustical couplant into the chamber in said ultrasound probe module;

(c) applying pressure to the liquid acoustical couplant which causes the liquid acoustical couplant to pass through the pores of said porous membrane;

(d) placing the porous membrane against a surface; and (e) activating the ultrasound probe.

17. The method of claim 16 wherein the surface in step (d) is skin.

18. The method of claim 16 wherein the porous membrane has a pore size in the range of about 0.01 μm to 0.2 μm and the liquid couplant material is selected from the group consisting of water, and mixtures of water and isopropanol.

19. The method of claim 18 where in the pressure is about 1–5 p.s.i.

20. The method of any one of claims 16, 18 or 19 wherein the surface in step (d) is a surface of an object having an opposing surface, and steps (a) through (e) are performed with regards to said opposing surface, step (e) being performed simultaneously with regards to both surfaces, one of said ultrasound probes functioning as an ultrasound transducer and the other ultrasound probe functioning as an ultrasound receiver.

21. The method of claim 16 wherein the surface in step (d) is a surface of an object having an opposing surface, the ultrasound probe functions as a receiver, and an ultrasound signal is initiated in the object by striking said opposing surface with a laser beam.

22. A method of performing an ultrasound test comprising the steps of:

(a) providing an assembly comprising: (i) an ultrasound probe and (ii) a cartridge attached to the ultrasound probe comprising a porous membrane attached to a second membrane to form a chamber containing a liquid acoustical couplant, the cartridge being attached to the ultrasound probe such that ultrasound waves traveling to or away from the ultrasound probe will pass through said chamber and porous membrane;

(b) placing the porous membrane against a surface;

(c) pressing on the ultrasound probe to force the liquid acoustical couplant to pass through the porous membrane; and (d) activating the ultrasound probe.

23. A method of performing an ultrasound test according to claim 22 wherein in steps a, b and c the porous membrane is flexible and comprises a material having acoustical wave transmission characteristics which are similar to those of a liquid couplant which is passable therethrough and said membrane having a rigid pressure resistant structure so as to behave like a tight-meshed multi-layered sieve.

* * * * *